(12) United States Patent
Salmon

(10) Patent No.: US 11,116,922 B2
(45) Date of Patent: Sep. 14, 2021

(54) SUPPORT FOR A BREATHING ASSISTANCE APPARATUS AND/OR ACCESSORIES

(71) Applicant: Fisher & Paykel Healthcare Limited, Auckland (NZ)

(72) Inventor: Andrew Paul Maxwell Salmon, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 235 days.

(21) Appl. No.: 15/824,869

(22) Filed: Nov. 28, 2017

(65) Prior Publication Data

US 2018/0147374 A1    May 31, 2018

Related U.S. Application Data

(60) Provisional application No. 62/427,540, filed on Nov. 29, 2016.

(51) Int. Cl.
| | | |
|---|---|---|
| *A61M 16/00* | (2006.01) | |
| *A61M 16/06* | (2006.01) | |
| *A61M 16/16* | (2006.01) | |
| A61M 16/20 | (2006.01) | |

(52) U.S. Cl.
CPC .... *A61M 16/0003* (2014.02); *A61M 16/0666* (2013.01); *A61M 16/16* (2013.01); *A61M 16/0605* (2014.02); *A61M 16/0683* (2013.01); *A61M 16/201* (2014.02); *A61M 2205/3368* (2013.01)

(58) Field of Classification Search
CPC ........ A61M 2209/08; A61M 2209/082; A61M 2209/084; A61M 2209/086; A61M 16/003; A61M 16/0666; A61M 16/16; A61M 16/0683; A61B 50/20; A61B 50/24; F16B 2200/30; F16M 11/04; F16M 2200/28
See application file for complete search history.

(56) References Cited

U.S. PATENT DOCUMENTS

| | | | |
|---|---|---|---|
| 3,915,164 A | * | 10/1975 | Bird ...................... A61M 16/00 128/204.25 |
| 4,515,283 A | | 5/1985 | Suzuki |
| 4,926,856 A | | 5/1990 | Cambio, Jr. et al. |
| 4,955,877 A | | 9/1990 | Kurtz et al. |

(Continued)

FOREIGN PATENT DOCUMENTS

| | | |
|---|---|---|
| DE | 10323754 | 12/2004 |
| DE | 102007026565 A1 | 12/2007 |

(Continued)

OTHER PUBLICATIONS

"New Power Cord for Respironics REMstar Plus, Pro, and Auto Machines", Amazon.com (Year: 2020).*

(Continued)

*Primary Examiner* — Margaret M Luarca
(74) *Attorney, Agent, or Firm* — Knobbe, Martens, Olson & Bear, LLP

(57) ABSTRACT

A holder apparatus for holding a conduit and/or patient interface such as a cannula, has a mount 251 to couple with a breathing assistance apparatus 10 and at least one mechanical feature 237a, 237b for holding the conduit and/or patient interface such as a cannula in place relative to the breathing assistance apparatus.

20 Claims, 23 Drawing Sheets

(56) References Cited

U.S. PATENT DOCUMENTS

| | | | |
|---|---|---|---|
| 6,427,984 B1 | 8/2002 | Mulvaney et al. | |
| 6,750,556 B2 | 6/2004 | Sodemann et al. | |
| 7,644,901 B2* | 1/2010 | Scheper | B63C 11/22 |
| | | | 248/311.2 |
| 7,942,380 B2 | 5/2011 | Bertinetti et al. | |
| 8,316,848 B2 | 11/2012 | Kwok et al. | |
| 8,540,196 B1* | 9/2013 | Hodson | F16L 3/012 |
| | | | 248/121 |
| 8,814,107 B2* | 8/2014 | Hampe | F16M 11/04 |
| | | | 248/121 |
| 9,072,543 B2 | 7/2015 | Miller et al. | |
| 9,182,062 B2 | 11/2015 | Kwok et al. | |
| 9,474,848 B2* | 10/2016 | Williams | A61M 3/0229 |
| 9,872,703 B2 | 1/2018 | Miller et al. | |
| 10,058,666 B2 | 8/2018 | Kwok et al. | |
| 2002/0043595 A1* | 4/2002 | Bridgers | A61M 16/08 |
| | | | 248/125.8 |
| 2005/0275178 A1* | 12/2005 | Huesdash | B62B 3/02 |
| | | | 280/47.35 |
| 2006/0144396 A1* | 7/2006 | DeVries | A61M 16/0057 |
| | | | 128/204.21 |
| 2007/0045152 A1 | 3/2007 | Kwok et al. | |
| 2009/0039210 A1* | 2/2009 | Yates | A61G 7/0503 |
| | | | 248/74.1 |
| 2010/0218764 A1 | 9/2010 | Kwok et al. | |
| 2011/0203587 A1 | 8/2011 | Bertinetti et al. | |
| 2014/0083524 A1 | 3/2014 | Huang | |
| 2016/0317392 A1 | 11/2016 | Harris et al. | |
| 2018/0132894 A1 | 5/2018 | Miller et al. | |
| 2018/0147374 A1 | 5/2018 | Salmon | |

FOREIGN PATENT DOCUMENTS

| | | |
|---|---|---|
| FR | 2901998 | 12/2007 |
| JP | 2016-135200 | 7/2016 |
| WO | WO2002/092157 | 11/2002 |
| WO | WO2004084981 | 10/2004 |
| WO | WO2004/112529 | 12/2004 |
| WO | WO2007019624 | 2/2007 |
| WO | WO2007/045905 | 4/2007 |
| WO | WO 2010/039051 | 4/2010 |
| WO | WO2015/068687 | 5/2015 |

OTHER PUBLICATIONS

"RespLabs CPAP Hose, Black-Out Tubing", Amazon.com (Year: 2020).*

Fisher & Paykel Healthcare Limited, myAIRVO Compact Stand (900PT400) User Instructions (revision B), 2010, in 2 pages.

Chinese Patent Office, First Office Action, Application No. 201721633735.3, dated Apr. 4, 2019, in 5 pages.

* cited by examiner

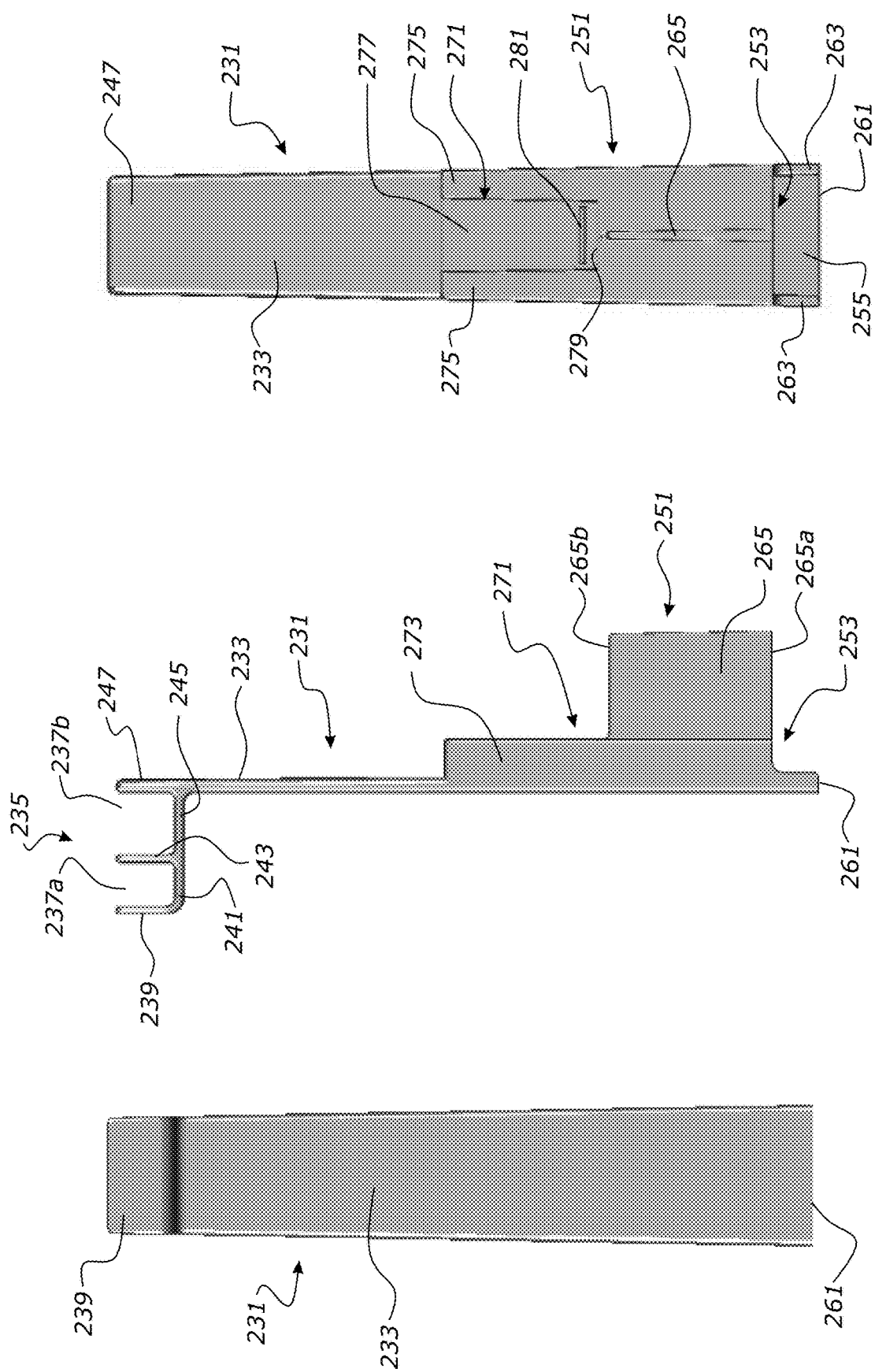

SUPPORT FOR A BREATHING ASSISTANCE APPARATUS AND/OR ACCESSORIES

TECHNICAL FIELD

The present invention relates to a support apparatus for a breathing assistance apparatus and/or for accessories of such an apparatus.

BACKGROUND ART

Breathing assistance apparatuses are used in various environments such as hospital, medical facility, residential care, or home environments to deliver a flow of gas to users or patients.

The breathing assistance apparatuses typically have one or more accessories such as a breathing conduit and a patient interface such as a cannula for delivering gases to a patient. The conduit is often a significant length to enable gases to be delivered from the housing of the breathing assistance apparatus to the patient who can be positioned a reasonable distance away from the apparatus. For example, the apparatus may be placed on a floor or other support surface, and the patient may be in a bed. Depending on the configuration of the breathing assistance apparatus, the apparatus may have additional accessories such as a flexible liquid bag that delivers liquid to a humidifier liquid chamber via one more tubes.

For home use, a breathing assistance apparatus may typically be kept on the floor because the apparatus may be large and noisy. Additionally, the apparatus is likely to be kept on the floor when the apparatus is not being used, so it can be positioned out of the way. The floor environment can be dusty, increasing the likelihood of dust and particulate ingress into the breathing assistance apparatus and potentially into the gasflow. Because the apparatus may have gases inlet(s) near the bottom of the apparatus, there may be a perception that the apparatus should not be positioned on the floor. Generally, breathing assistance apparatuses do not provide adequate storage for the patient interface such as a cannula when it is not being used, meaning that the used patient interface such as a cannula needs to be placed on a support surface such as a bedside table when it is not being used. Additionally, the conduit can present a tripping hazard. Similar issues may be encountered in a transport situation; e.g. helicopter or ambulance use.

SUMMARY

Accordingly, it would be desirable to provide a holder and/or storage for at least one accessory of a breathing assistance apparatus, such as a conduit and/or patient interface such as a cannula.

Additionally or alternatively, it would be desirable to provide a support apparatus for a breathing assistance apparatus that enables the breathing assistance apparatus to be stored above a support surface.

It is an object of one or more of the disclosed embodiments to provide a support or holder for a breathing assistance apparatus and/or accessories that goes at least some way toward achieving one of the above desirable outcomes, or that at least provides the public or a medical professional with a useful choice.

Thus, in accordance with certain features, aspects and advantages of at least one of the embodiments disclosed herein, a holder apparatus for holding a conduit and/or patient interface is disclosed, the holder apparatus comprising: a mount to couple with a breathing assistance apparatus; and at least one mechanical feature for holding the conduit and/or patient interface such as a cannula in place relative to the breathing assistance apparatus.

In some configurations, the holder apparatus comprises an upstanding holder, wherein the upstanding holder comprises said at least one mechanical feature for holding a conduit and/or patient interface such as a cannula, and wherein the at least one mechanical feature has a shape that is complementary to the shape of the conduit and/or patient interface such as a cannula.

In some configurations, the at least one mechanical feature comprises one or more of: a recess or groove; a clip; a hinge mechanism; a compliant sling or strap; a hook and loop fastener.

In some configurations, the holder apparatus comprises a plurality of the mechanical features. In some configurations, the mechanical features are configured to hold the conduit and the patient interface such as a cannula.

In some configurations, the holder apparatus is upstanding and is configured such that mechanical feature(s) is/are located higher than the breathing assistance apparatus or at or adjacent a top of the breathing assistance apparatus, when the mount is coupled with the breathing assistance apparatus.

In some configurations, a portion of the holder apparatus is upstanding and is configured such that a power cord can be wrapped around the portion between the portion and the breathing assistance apparatus.

In some configurations, the holder apparatus further comprises an additional mechanical feature for holding a liquid bag. In some configurations, the additional mechanical feature is positioned vertically higher than the mechanical feature(s) for holding the conduit and/or patient interface such as a cannula.

Additionally, in accordance with certain features, aspects and advantages of at least one of the embodiments disclosed herein, the combination of the holder apparatus as outlined above and a breathing assistance apparatus with a conduit and/or patient interface such as a cannula is disclosed, wherein the holder apparatus is coupled with the breathing assistance apparatus, and wherein the conduit and/or patient interface such as a cannula is/are held in place relative to the holder apparatus by the mechanical feature(s).

In some configurations, the breathing assistance apparatus comprises a conduit and a patient interface such as a cannula, and the holder apparatus comprises a plurality of the mechanical features, wherein the conduit is held in place by one of the mechanical features and the patient interface such as a cannula is held in place by another of the mechanical features.

In some configurations, the holder apparatus is positioned on a support surface, and the conduit and/or patient interface such as a cannula is/are held above the support surface by the holder apparatus.

Additionally, in accordance with certain features, aspects and advantages of at least one of the embodiments disclosed herein, a support apparatus for a breathing apparatus is disclosed, the support apparatus comprising: a stand; and a holder, wherein the holder comprises at least one mechanical feature for holding a conduit and/or patient interface such as a cannula of the breathing assistance apparatus in place; wherein the stand is configured to support the holder in an upstanding configuration; and wherein the stand and/or the holder is/are configured to support the breathing assistance apparatus.

In some configurations, the holder extends upwardly from a periphery of the stand.

In some configurations, the holder comprises a mount that is configured to releasably couple the support apparatus with the breathing assistance apparatus. In some configurations, the mount is additionally configured to couple the stand with the holder. That is, the mount may be a dual mount. In some configurations, the stand comprises a base and an upstand, wherein the upstand is configured to couple with the mount.

In some configurations, the position of the mount on the holder is such that an underside of the breathing assistance apparatus will be positioned with a spacing above a top surface of a base of the stand, when the breathing assistance apparatus is coupled with the support apparatus.

In some configurations, the holder comprises a plurality of the mechanical features for holding a conduit and a patient interface such as a cannula.

In some configurations, the mechanical feature(s) is/are positioned on the holder such that the conduit and/or patient interface such as a cannula is/are held above a support surface when held by the mechanical feature(s).

In some configurations, the support apparatus further comprises an additional mechanical feature for holding a liquid bag. In some configurations, the additional mechanical feature is positioned vertically higher than the mechanical feature(s) for holding the conduit and/or patient interface such as a cannula.

Additionally, in accordance with certain features, aspects and advantages of at least one of the embodiments disclosed herein, the combination of the support apparatus as outlined above and a breathing assistance apparatus with a conduit and/or patient interface such as a cannula is disclosed, wherein the breathing assistance apparatus is supported by the support apparatus, and wherein the conduit and/or patient interface such as a cannula is/are held in place relative to the breathing assistance apparatus by the mechanical feature(s).

In some configurations, the breathing assistance apparatus comprises a conduit and a patient interface such as a cannula, and the support apparatus comprises a plurality of mechanical features, wherein the conduit is held in place by one of the mechanical features and the patient interface such as a cannula is held in place by another of the mechanical features.

In some configurations, the support apparatus is positioned on a support surface, and the conduit and/or patient interface such as a cannula is/are held above the support surface by the support apparatus.

In some configurations, the breathing assistance apparatus is positioned on the stand. In some configurations, the breathing assistance apparatus and/or the stand comprise one or more engagement features to locate the breathing assistance apparatus on the stand. In some configurations, the engagement features comprise a plurality of pins and recesses.

In some configurations, an underside of the breathing assistance apparatus is positioned with a spacing above a top surface of a base of the stand.

Additionally, in accordance with certain features, aspects and advantages of at least one of the embodiments disclosed herein, a holder apparatus for holding a conduit and/or patient interface such as a cannula is disclosed, the holder apparatus comprising: a mount to couple with a breathing assistance apparatus; and an upstanding holder, wherein the upstanding holder comprises at least one mechanical feature for holding a conduit and/or patient interface such as a cannula, wherein the at least one mechanical feature has a shape that is complementary to the shape of the conduit and/or patient interface such as a cannula.

In some configurations, the at least one mechanical feature comprises two recesses, with one of the recesses configured to receive the conduit and the other of the recesses configured to receive the patient interface such as a cannula.

In some configurations, the at least one mechanical feature comprises one or more compliant slings.

In some configurations, the at least one mechanical feature comprises one or more clips.

In some configurations, the at least one mechanical feature comprises one or more hook and loop fasteners that is/are configured to secure around the conduit and/or patient interface such as a cannula to hold the conduit and/or patient interface such as a cannula in position.

Additionally, in accordance with certain features, aspects and advantages of at least one of the embodiments disclosed herein, the combination of the holder apparatus as outlined above and a breathing assistance apparatus with a conduit and/or patient interface such as a cannula is disclosed, wherein the breathing assistance apparatus is coupled to the mount of the holder apparatus, and wherein the conduit and/or patient interface such as a cannula is/are held in place by the mechanical feature(s).

In some configurations, the breathing assistance apparatus comprises a conduit and a patient interface such as a cannula, and the holder apparatus comprises a plurality of mechanical features, wherein the conduit and patient interface such as a cannula are held in place by respective mechanical features.

In some configurations, the conduit and/or patient interface such as a cannula is/are held above a support surface by the holder apparatus.

Additionally, in accordance with certain features, aspects and advantages of at least one of the embodiments disclosed herein, a support apparatus for a breathing apparatus is disclosed, the support apparatus comprising: a base; an upstanding component; and a mount on the upstanding component with a spacing provided between the base and the mount, wherein the mount is configured to releasably couple the support apparatus with the breathing assistance apparatus such that an underside of the breathing assistance apparatus is positioned with a spacing above the base.

In some configurations, the upstanding component is removably coupled to the base. In some alternative configurations, the upstanding component may be integrally formed with the base.

In some configurations, the upstanding component is removably coupled to the base by the mount. That is, the mount may be a dual mount.

In some configurations, the base has a relatively small vertical dimension and relatively large horizontal dimensions, and a top face of the base comprises a recess for storage of one or more accessories.

In some configurations, the base further comprises a support member spaced from the mount to assist with supporting the breathing assistance apparatus above the base. In some configurations, the support member is positioned at or adjacent to an opposite side of the base to the mount. In some configurations, the support member comprises an upwardly projecting member.

Additionally, in accordance with certain features, aspects and advantages of at least one of the embodiments disclosed herein, the combination of the support apparatus as outlined above and a breathing assistance apparatus is disclosed, wherein the breathing assistance apparatus is releasably coupled to the mount, and wherein an underside of the breathing assistance apparatus is positioned with a spacing above a top surface of the base.

In some configurations, the spacing is sufficient to provide a storage space for a liquid bag, breathing conduit, and/or power cord of the breathing assistance apparatus.

In some configurations, the support apparatus and breathing apparatus comprise complementary fastening features that clip the breathing assistance apparatus to the mount. In some configurations, the complementary fastening features comprise an indented portion on one of the support apparatus and the breathing assistance apparatus, and a complementary projecting portion on the other of the support apparatus and the breathing assistance apparatus.

Additionally, in accordance with certain features, aspects and advantages of at least one of the embodiments disclosed herein, a support apparatus is disclosed, the support apparatus comprising: a holder and/or a stand; and a mount on the holder and/or stand to releasably couple the holder and/or stand with a breathing assistance apparatus, wherein the mount comprises at least one alignment feature to align the mount with a complementary mount of the breathing assistance apparatus, and wherein the mount further comprises a connection feature to releasably fasten the support apparatus to the breathing assistance apparatus.

In some configurations, the support apparatus comprises both the holder and the stand. In some alternative configurations, the support apparatus comprises the holder but no stand. In some alternative configurations, the support apparatus comprises the stand but no holder.

In some configurations, the mount is provided on the holder. In some alternative configurations, the mount is provided on the stand. In some alternative configurations, the mount is provided on both the holder and the stand.

In some configurations, the at least one alignment feature is/are arranged to engage with a corresponding tongue on the breathing assistance apparatus.

In some configurations, the at least one alignment feature comprises opposed slots into which corresponding feature(s) from the breathing assistance apparatus are receivable. In some configurations, the opposed slots are arranged to receive opposite sides of a tongue on the breathing assistance apparatus.

In some configurations, the connection feature comprises a protrusion to engage with a corresponding protrusion on a tongue of the breathing assistance apparatus.

Additionally, in accordance with certain features, aspects and advantages of at least one of the embodiments disclosed herein, the combination of the support apparatus as outlined above and a breathing assistance apparatus is disclosed, wherein the breathing assistance apparatus is releasably coupled to the support apparatus.

Additionally, in accordance with certain features, aspects and advantages of at least one of the embodiments disclosed herein, a support apparatus is disclosed, the support apparatus comprising: a stand; a holder for holding a conduit and/or a patient interface such as a cannula; and a dual mount to releasably couple the holder to the stand and to releasably couple the holder to a breathing assistance apparatus; and wherein the stand comprises a base and an upstand, wherein the dual mount is configured to releasably couple with the upstand.

In some configurations, the upstand is configured to receive, or be received, in the dual mount. In some configurations, the upstand is configured to be received in a receptacle in the dual mount. In some configurations, the receptacle comprises a stop to prevent over-insertion of the upstand into the receptacle.

Features from one or more embodiments or configurations may be combined with features of one or more other embodiments or configurations. Additionally, more than one embodiment may be used together during a process of respiratory support of a patient.

The term 'comprising' as used in this specification means 'consisting at least in part of'. When interpreting each statement in this specification that includes the term 'comprising', features other than that or those prefaced by the term may also be present. Related terms such as 'comprise' and 'comprises' are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

It should be understood that alternative embodiments or configurations may comprise any or all combinations of two or more of the parts, elements or features illustrated, described or referred to in this specification.

This invention may also be said broadly to consist in the parts, elements and features referred to or indicated in the specification of the application, individually or collectively, and any or all combinations of any two or more said parts, elements or features.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth.

BRIEF DESCRIPTION OF THE DRAWINGS

Specific embodiments and modifications thereof will become apparent to those skilled in the art from the detailed description herein having reference to the figures that follow, of which:

FIG. 20 is a left side view of the holder.

FIG. 21 is a front view of the holder.

FIG. 22 is a right-side view of the holder.

DETAILED DESCRIPTION OF SPECIFIC EMBODIMENTS

1. Introduction

Figure 1:
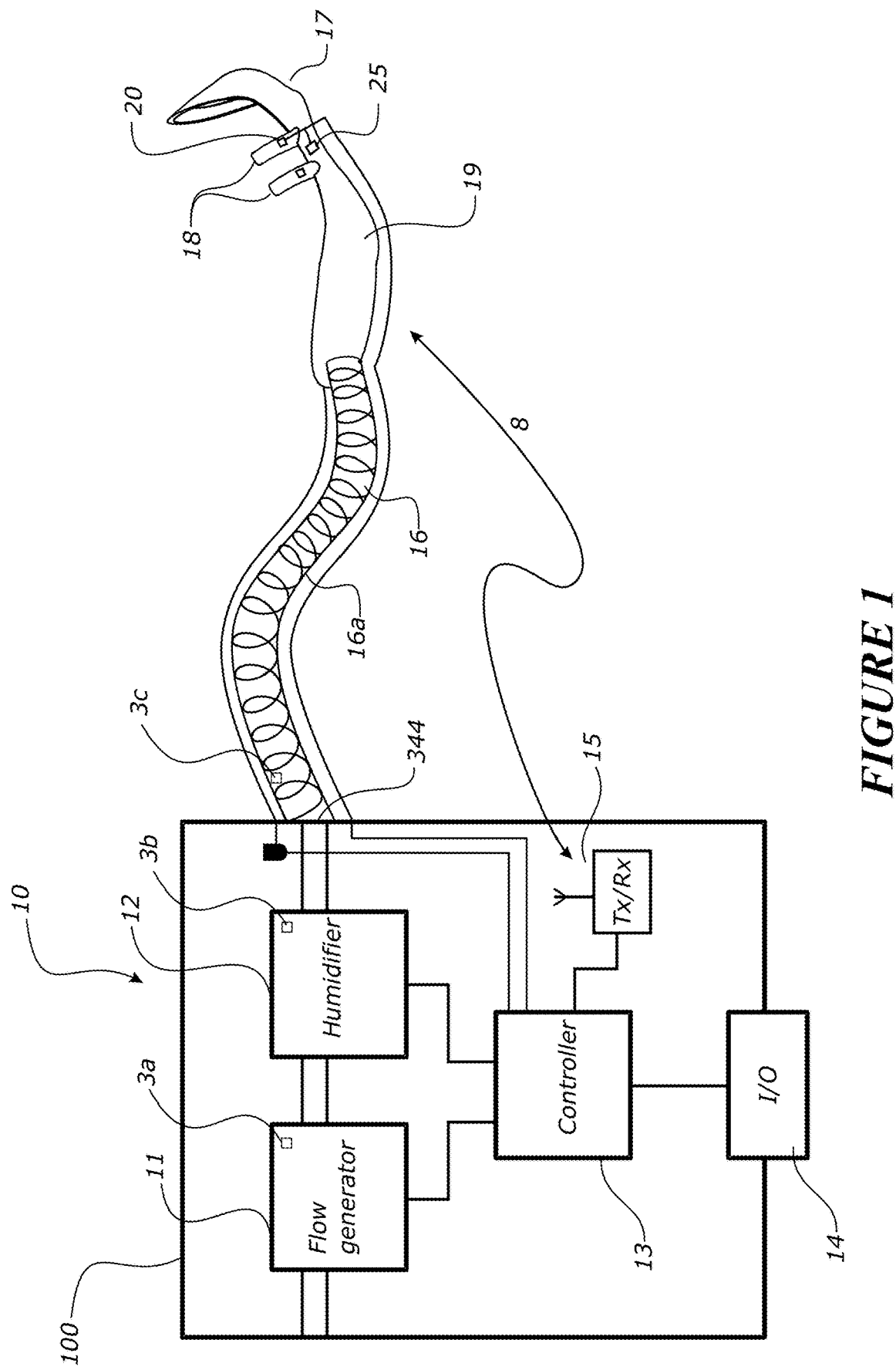
FIG. 1 shows in diagrammatic form a breathing assistance apparatus in the form of a flow therapy apparatus.

A flow therapy apparatus 10 for delivering a flow of gas to a patient is shown in FIG. 1. In general terms, the apparatus 10 comprises a main housing 100 that contains a flow generator 11 in the form of a motor/impeller arrangement, an optional humidifier 12, a controller 13, and a user I/O interface 14 (comprising, for example, a display and input device(s) such as button(s), a touch screen, or the like). The controller 13 is configured or programmed to control the components of the apparatus, including: operating the flow generator 11 to create a flow of gas (gas flow) for delivery to a patient, operating the humidifier 12 (if present) to humidify and/or heat the generated gas flow, receive user input from the user interface 14 for reconfiguration and/or user-defined operation of the apparatus 10, and output information (for example on the display) to the user. The user could be a patient, healthcare professional, or anyone else interested in using the apparatus.

A patient breathing conduit 16 is coupled to a gas flow output 344 in the housing 100 of the flow therapy apparatus 10, and is coupled to a patient interface 17 such as a nasal cannula with a manifold 19 and nasal prongs 18. Additionally, or alternatively, the patient breathing conduit 16 could be coupled to a face mask. Additionally or alternatively, the patient breathing conduit could be coupled to a nasal pillows mask, and/or a nasal mask, and/or a tracheostomy interface, or any other suitable type of patient interface. The gas flow, which may be humidified, that is generated by the flow therapy apparatus 10 is delivered to the patient via the patient breathing conduit 16 through the cannula 17. The patient breathing conduit 16 can have a heater wire 16a to heat gas flow passing through to the patient. The heater wire 16a is under the control of the controller 13. The patient breathing conduit 16 and/or patient interface 17 can be considered part of the flow therapy apparatus 10, or alternatively peripheral to it. The flow therapy apparatus 10, breathing conduit 16, and patient interface 17 together form a flow therapy system.

General operation of a flow therapy breathing apparatus 10 will be known to those skilled in the art, and need not be described in detail here. However, in general terms, the controller 13 controls the flow generator 11 to generate a gas flow of the desired flow rate, controls one or more valves to control the mix of air and oxygen or other alternative gas, and controls the humidifier 12 if present to humidify the gas flow and/or heat the gas flow to an appropriate level. The gas flow is directed out through the patient breathing conduit 16 and cannula 17 to the patient. The controller 13 can also control a heating element in the humidifier 12 and/or the heating element 16a in the patient breathing conduit 16 to heat the gas to a desired temperature that achieves a desired level of therapy and/or comfort for the patient. The controller 13 can be programmed with, or can determine, a suitable target temperature of the gas flow.

Operation sensors 3a, 3b, 3c, 20, and 25, such as flow, temperature, humidity, and/or pressure sensors, can be placed in various locations in the flow therapy apparatus 10 and/or the patient breathing conduit 16 and/or cannula 17. Output from the sensors can be received by the controller 13, to assist it to operate the flow therapy apparatus 10 in a manner that provides optimal therapy. In some configurations, providing optimal therapy includes meeting a patient's inspiratory demand. The apparatus 10 may have a transmitter and/or receiver 15 to enable the controller 13 to receive signals 8 from the sensors and/or to control the various components of the flow therapy apparatus 10, including but not limited to the flow generator 11, humidifier 12, and heater wire 16a, or accessories or peripherals associated with the flow therapy apparatus 10. Additionally, or alternatively, the transmitter and/or receiver 15 may deliver data to a remote server or enable remote control of the apparatus 10.

The flow therapy apparatus 10 may be any suitable type of apparatus, but in some configurations may deliver a high gas flow or high flow therapy (of e.g. air, oxygen, other gas mixture, or some combination thereof) to a patient to assist with breathing and/or treat breathing disorders. In some configurations, the gas is or comprises oxygen. In some configurations, the gas comprises a blend of oxygen and ambient air. 'High flow therapy' as used in this disclosure may refer to delivery of gases to an adult patient at a flow rate of greater than or equal to about 10 liters per minute (10 LPM), or to a neonatal, infant, or child patient at a flow rate of greater than or equal to about 1 liter per minute (1 LPM). In some configurations, for an adult patient 'high flow therapy' may refer to the delivery of gases to a patient at a flow rate of between about 10 LPM and about 100 LPM, or between about 15 LPM and about 95 LPM, or between about 20 LPM and about 90 LPM, or between about 25 LPM and about 85 LPM, or between about 30 LPM and about 80 LPM, or between about 35 LPM and about 75 LPM, or between about 40 LPM and about 70 LPM, or between about 45 LPM and about 65 LPM, or between about 50 LPM and about 60 LPM. In some configurations, for a neonatal, infant, or child patient 'high flow therapy' may refer to the delivery of gases to a patient at a flow rate of greater than about 1 LPM, or between about 1 LPM and about 25 LPM, or between about 2 LPM and about 25 LPM, or between about 2 LPM and about 5 LPM, or between about 5 LPM and about 25 LPM, or between about 5 LPM and about 10 LPM, or between about 10 LPM and about 25 LPM, or between about 10 LPM and about 20 LPM, or between about 10 LPM and 15 LPM, or between about 20 LPM and about 25 LPM. Therefore, a high flow therapy apparatus for use with either an adult patient or a neonatal, infant, or child patient, may deliver gases to the patient at a flow rate of between about 2 LPM and about 100 LPM, or at a flow rate in any of the sub-ranges outlined above. Gases delivered may comprise a percentage of oxygen. In some configurations, the percentage of oxygen in the gases delivered may be between about 20% and about 100%, or between about 30% and about 100%, or between about 40% and about 100%, or between about 50% and about 100%, or between about 60% and about 100%, or between about 70% and about 100%, or between about 80% and about 100%, or between about 90% and about 100%, or about 100%, or 100%.

High flow therapy has been found effective in meeting or exceeding the patient's inspiratory demand, increasing oxygenation of the patient and/or reducing the work of breathing. Additionally, high flow therapy may generate a flushing effect in the nasopharynx such that the anatomical dead space of the upper airways is flushed by the high incoming gas flows. This creates a reservoir of fresh gas available for each and every breath, while minimising re-breathing of carbon dioxide, nitrogen, etc.

The patient interface may be a non-sealing interface to prevent barotrauma (e.g. tissue damage to the lungs or other organs of the respiratory system due to difference in pressure relative to the atmosphere). The patient interface may be a nasal cannula with a manifold and nasal prongs, and/or a face mask, and/or a nasal pillows mask, and/or a nasal mask, and/or a tracheostomy interface, or any other suitable type of patient interface.

As described below, the flow therapy apparatus 10 has various features to assist with the functioning, use, and/or configuration of the apparatus 10.

2. Overview of Breathing Assistance Apparatus

Figure 2:
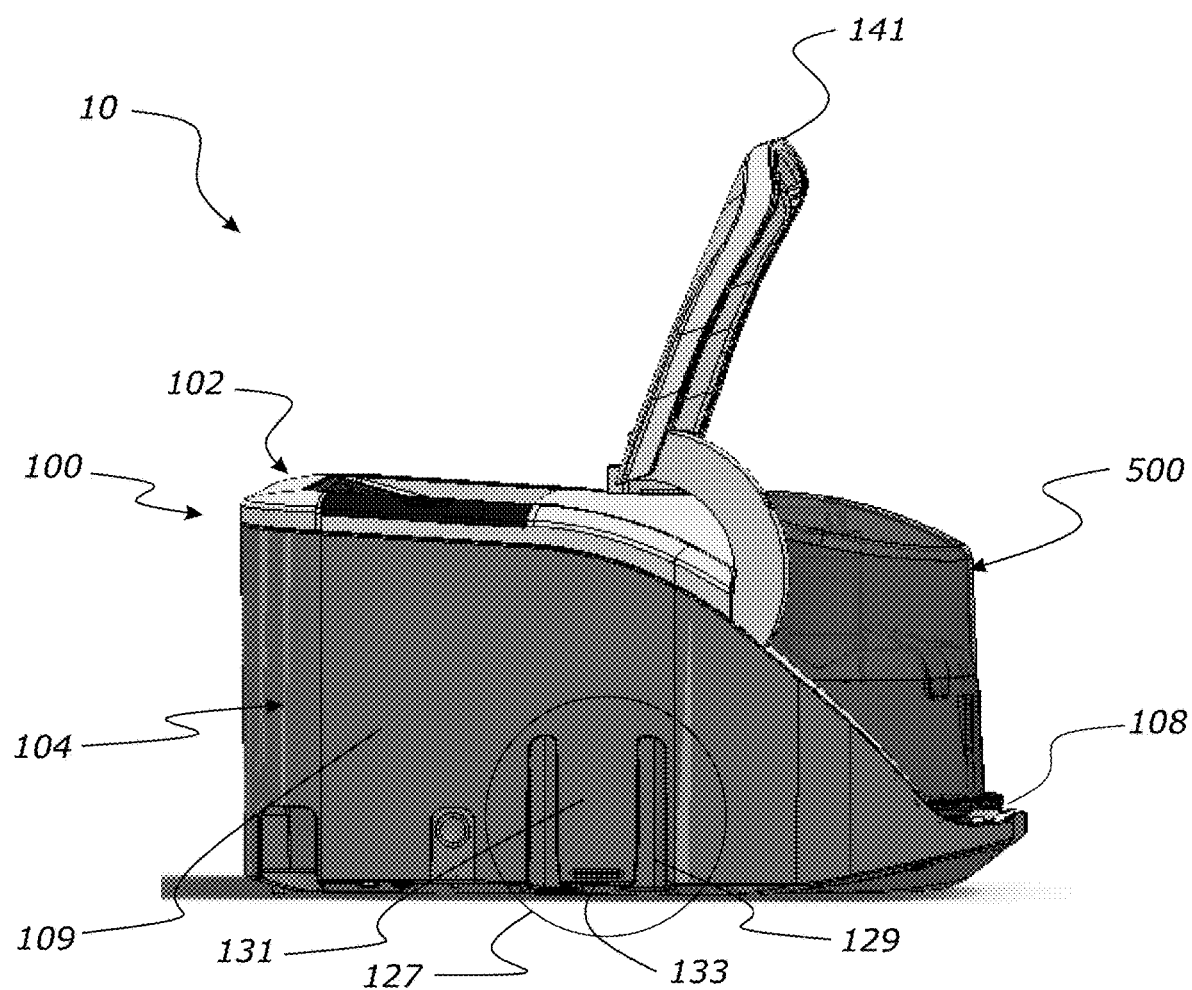
FIG. 2 is a left side view of the flow therapy apparatus showing an exemplary location of and integral mount for coupling the breathing assistance apparatus to a support.

As shown in FIG. 2, the flow therapy apparatus 10 comprises a main housing 100. The main housing 100 has a main housing upper chassis 102 and a main housing lower chassis 104.

The main housing has a peripheral wall arrangement. The peripheral wall arrangement defines a humidifier or liquid chamber bay 108 for receipt of a removable liquid chamber 500. The removable liquid chamber 500 contains a suitable liquid such as water for humidifying gases that will be delivered to a patient.

The apparatus 10 has a tiltable handle/lever 141 that enables a user to lift and carry the apparatus when in a raised position (FIG. 2), and that assists with maintaining the liquid chamber 500 in engagement with the housing 100 when in a lowered position.

In the form shown, the main housing lower chassis 104 peripheral wall arrangement comprises a substantially vertical left side outer wall 109 that is oriented in a front-to-rear direction of the main housing 100, a substantially vertical right side outer wall 111 (FIG. 3), and a substantially vertical rear outer wall 113 that extends between and connects the walls 109, 111. A bottom wall 115 extends between and connects the lower ends of walls 109, 111, 113, and forms a base of the apparatus and a substantially horizontal floor portion of the liquid chamber bay.

The floor portion of the liquid chamber bay 108 has a recess to receive a heater arrangement such as a heater plate or other suitable heating element(s) for heating liquid in the liquid chamber 500 for use during a humidification process.

The main housing lower chassis 104 is attachable to the upper chassis 102, either by suitable fasteners or integrated attachment features such as clips for example. When the main housing lower chassis 104 is attached to the main housing upper chassis 102, the walls of the upper and lower chassis engage with each other.

The apparatus has tongue and groove arrangements between components of the apparatus to reduce water and oxygen ingress into the unit. The apparatus advantageously has tongue and groove arrangements between the upper edges of the lower chassis walls and the lower edges of the upper chassis walls. The tongue and groove arrangements provide a substantially continuous liquid/gas flow-resistant coupling around the periphery of the upper and lower chassis parts 102, 104. For example, the lower chassis walls may be provided with grooves and the upper chassis walls may be provided with complementary tongues that are configured to be at least partly received in the respective grooves when the upper and lower chassis parts are assembled together. The continuous coupling advantageously extends along the front, sides, and at least most of the rear of the chassis parts, as shown, including around any corners between those surfaces.

The described configurations and orientations are examples only, and any suitable combination of the tongue and groove arrangements and/or orientations of the tongue and groove arrangements may be used in the apparatus.

Figure 3:
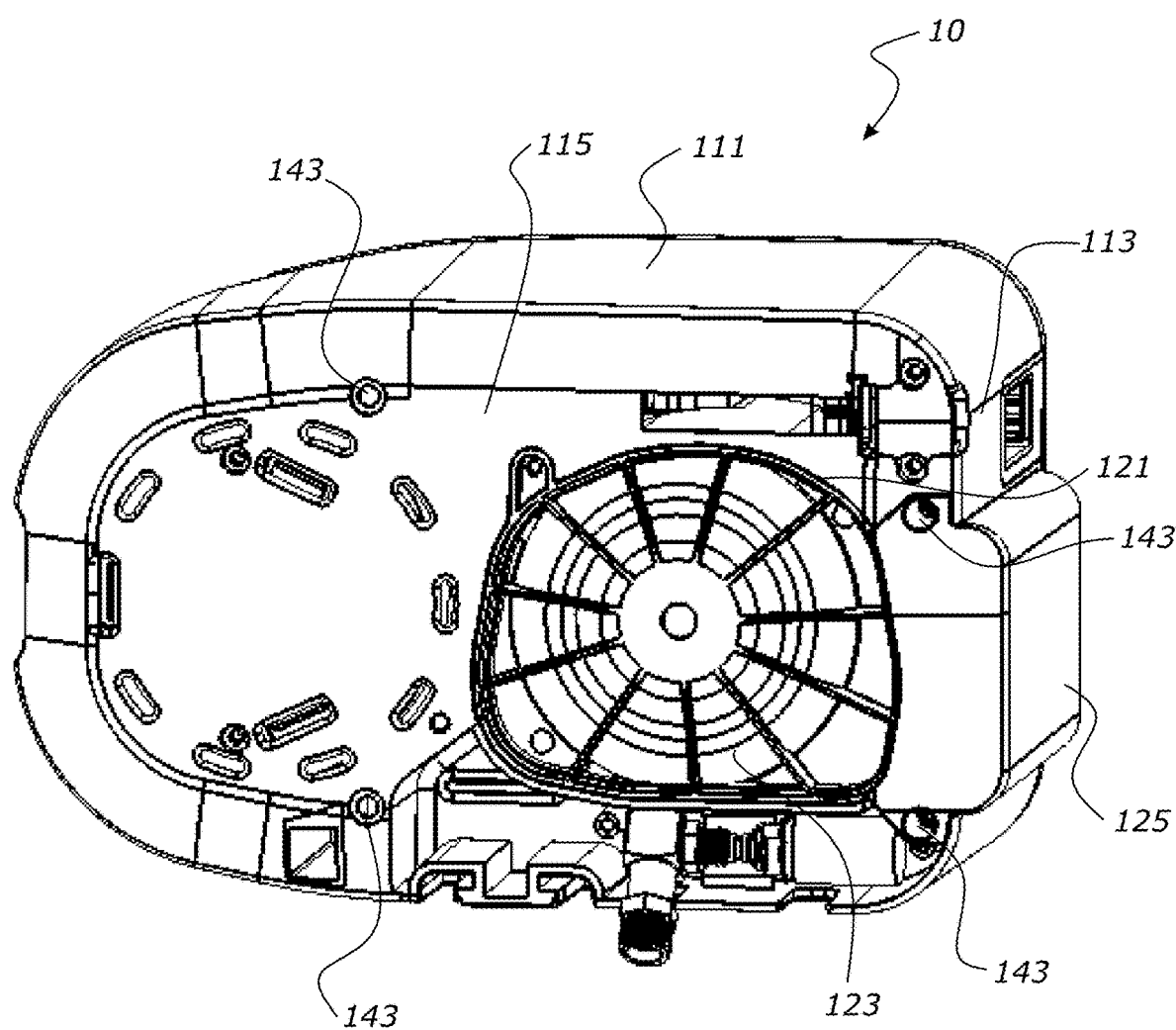
FIG. 3 is an underside perspective view of the flow therapy apparatus.

As shown in FIG. 3, the lower chassis 104 has a motor recess 121 for receipt of a removable motor and/or sensor module. A recess opening is provided in the bottom wall 115 adjacent a rear edge thereof, for receipt of the removable motor/sensor module. FIG. 3 shows a base 123 of the motor and/or sensor module that covers the opening into the motor recess 121. The motor and/or sensor module comprises a motor that forms a blower to cause gasflow, and may comprise one or more sensors to sense properties of the gas passing through the motor and/or sensor module.

The motor and/or sensor module and housing of the apparatus 10 are provided with suitable tubes and/or gasflow passages to deliver gases from one or more gases inlets of the apparatus, to a gases inlet port of the liquid chamber 500 to humidify the gases. The gases are delivered from a gases outlet port of the liquid chamber 500 to the patient outlet port 344 and thereby to the patient via the patient breathing conduit 16 and patient interface.

In the form shown, the motor recess 121 comprises a recess opening in a bottom wall of the housing. Alternatively, the recess opening could be in a different part of the housing, such as a side, front, or top of the housing.

The apparatus 10 may have a battery 125 to provide power to the apparatus when there is a power outage or for portable use. The battery may be replaceable.

In the form shown, the battery is coupled to an exterior of the back wall of the apparatus. This provides a large surface area to cool the battery and reduces the amount of heat entering the apparatus from the battery. Additionally, this configuration reduces the influence of heat generated by components of the apparatus on the battery, particularly when the battery is being charged. In an alternative configuration, the battery may be internally mounted in the main housing.

As shown in FIG. 2, the apparatus 10 has a mount 127 for mounting the apparatus to a support as will be described in more detail below with reference to FIGS. 4 to 29.

The mount 127 may be integrally formed with part of the main housing of the apparatus. In the form shown, the mount 127 is integrally formed with the left side wall 109 the lower chassis 104 of the housing. The mount 127 could instead be integrally formed with any of the other walls of the housing, such as a rear wall, right side wall, or other wall.

The side of the apparatus corresponding to the mount 127 comprises a recess 129. A downwardly projecting tongue 131 of the mount 127 has an upper end that is integrally formed with the wall, and is positioned in the recess. A free, lower end of the tongue 131 is provided with a protrusion in the form of a projecting bump 133. The bump projects outwardly a greater distance than the remainder of the tongue.

The main housing of the apparatus may be formed from any suitable material that will allow the mount 127 to be integrally formed. For example, the case may be formed from polycarbonate.

The integral mount 127 has greater impact strength compared to an additional, screwed in part. Strengthening of the mount 127 may also be done by, for example, varying the wall thickness, ribbing, or varying internal geometries.

3. Support Assembly

FIGS. 4 to 39 show exemplary configurations of a support and holder apparatus comprising a support assembly 200, 300, 400, 400' that can be used to support and hold the apparatus 10 and/or accessories of the apparatus, such as the conduit 16, patient interface such as a cannula 17, a power cord of the apparatus 10, and/or tubes from a liquid bag for delivering liquid to the liquid chamber 500 for example.

The support assembly 200 of FIGS. 4 to 27f comprises a stand 201 and a holder 231.

The stand 201 comprises a horizontally enlarged base 203 having a relatively small vertical dimension and relatively large horizontal dimensions. The base 203 comprises an upper surface 205 and a peripheral wall 207 that extends downwardly from the upper surface 205. The shape of the periphery of the upper surface 205 corresponds substantially to the shape of the housing of the breathing assistance apparatus 10 in plan view. While in the form shown the base 203 has a generally oblong shape in plan view, the shape of the base 203 may change depending on the shape of the housing of the breathing assistance apparatus 10 that will be supported.

The underside of the base 203 of the stand 201 comprises an under surface 209 and a plurality of strengthening ribs 211. The ribs may be any suitable shape or configuration to provide strength and rigidity to the base 203. A bottom edge 213 of the peripheral wall 207 is arranged to contact a support surface such as a floor, to support the support assembly 200 on the floor. If the strengthening ribs 211 are of the same depth as the peripheral wall 207, the bottom edges of the strengthening ribs will also contact the support surface.

The upper surface 205 of the base 203 surrounds a recess 215 for storage of one or more accessories of the breathing assistance apparatus 10. In the form shown, the recess 215 has a depth of a few millimetres. However, in different configurations, the upper surface 205 could be defined by one or more walls that extend(s) upwardly from a periphery of the recess 215, to provide a deeper recess. In other configurations, the recess 215 may not be provided, and the upper surface 205 of the base may be substantially planar.

Figure 12:
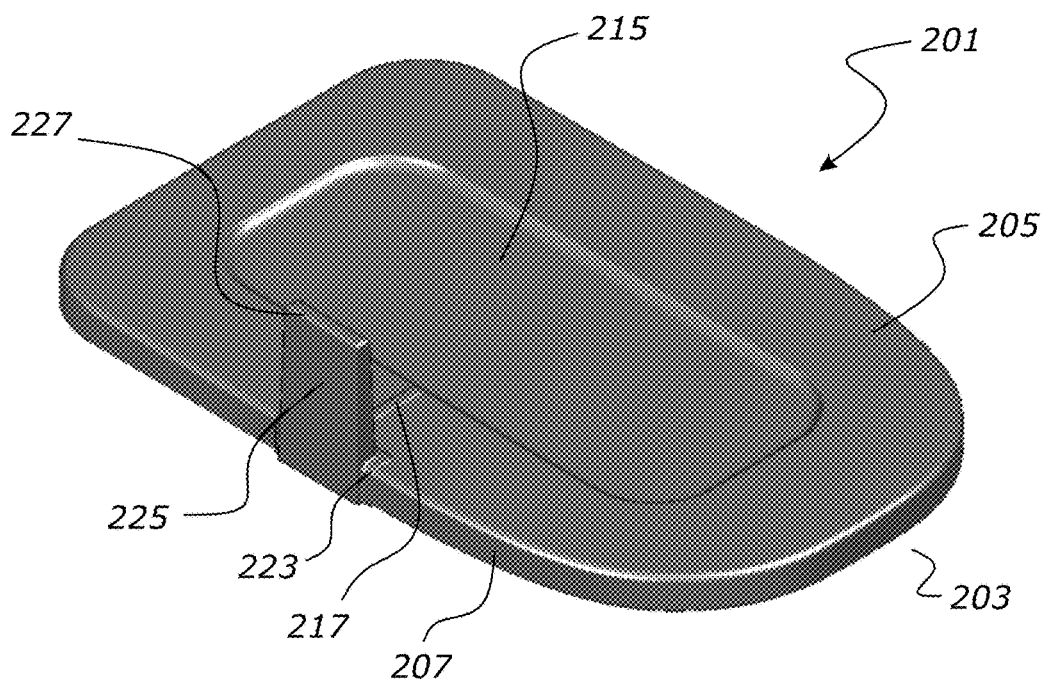
FIG. 12 is a left/front overhead perspective view of a stand of the support assembly.
Figure 13:
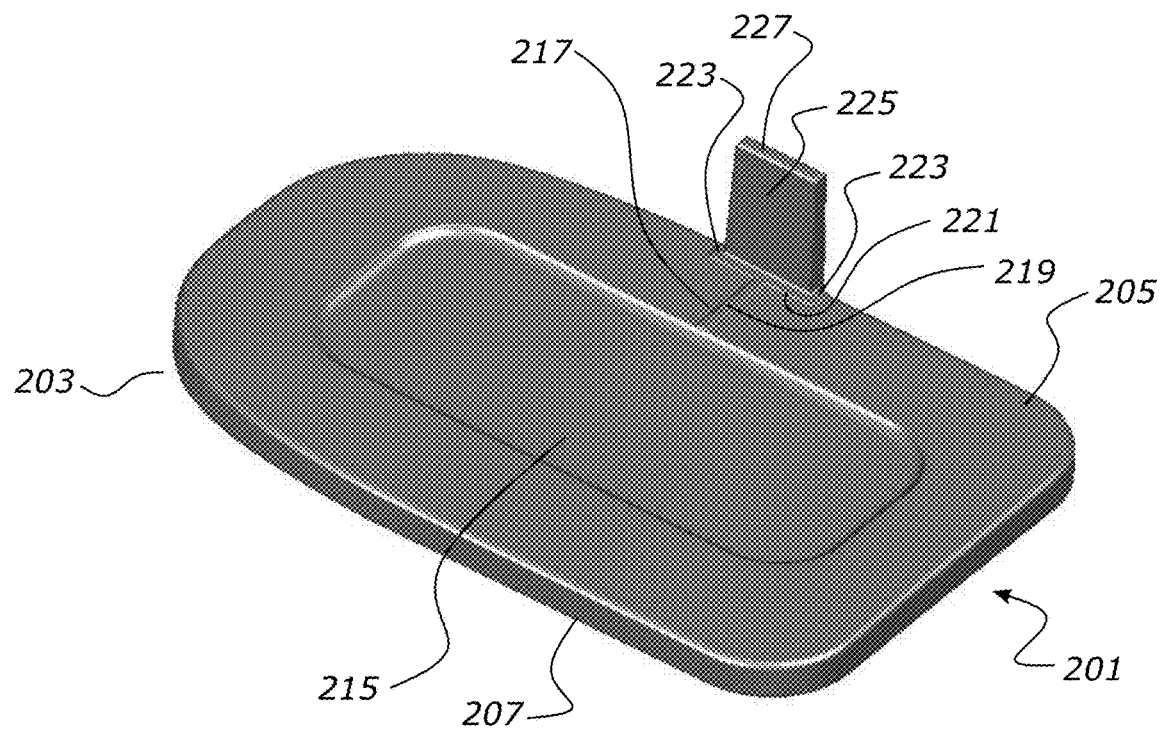
FIG. 13 is a right/rear overhead perspective view of the stand.
Figure 14:
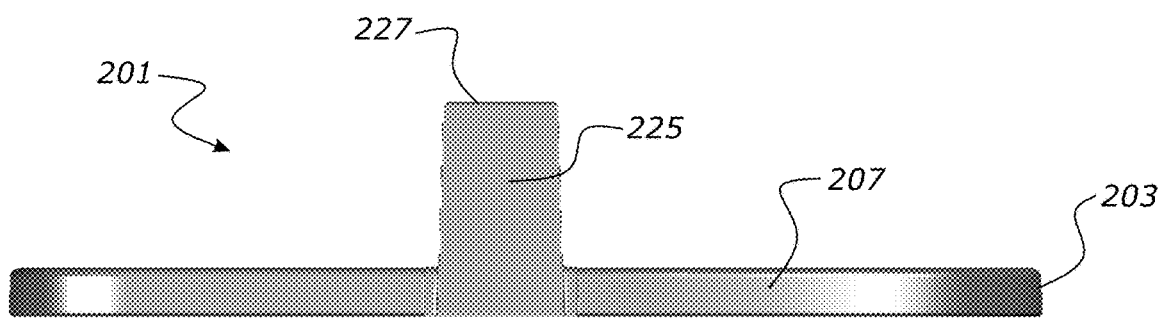
FIG. 14 is a left side view of the stand.
Figure 15:
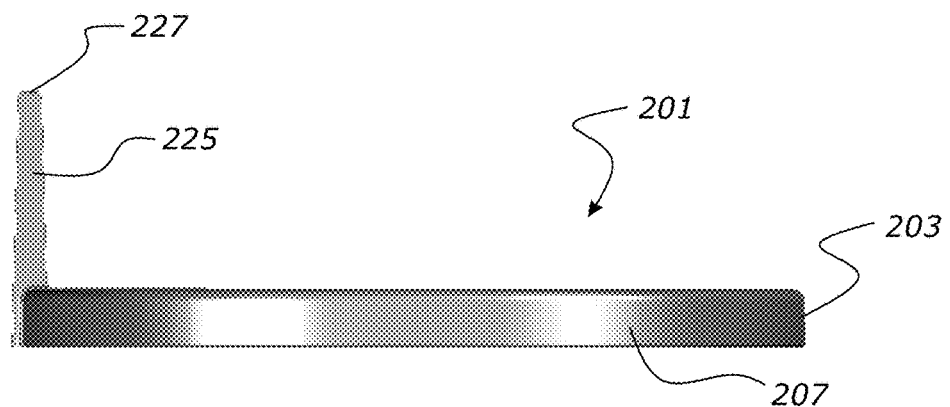
FIG. 15 is a front view of the stand.
Figure 16:
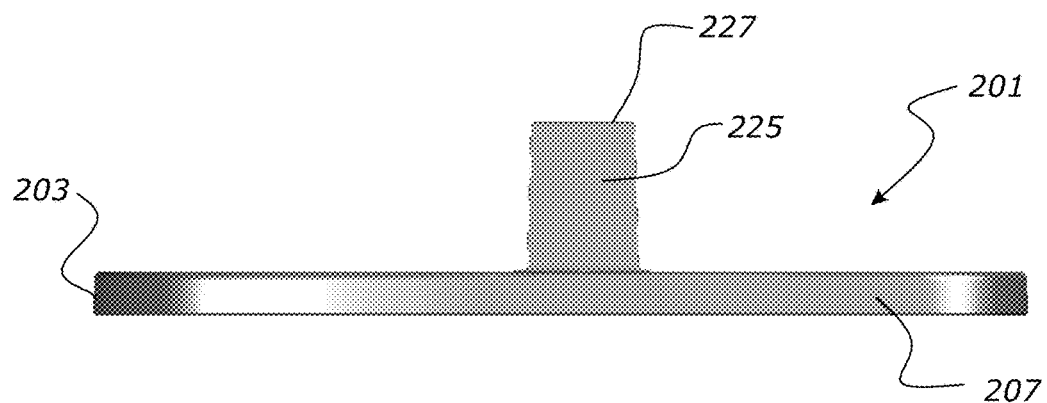
FIG. 16 is a right side view of the stand.
Figure 17:
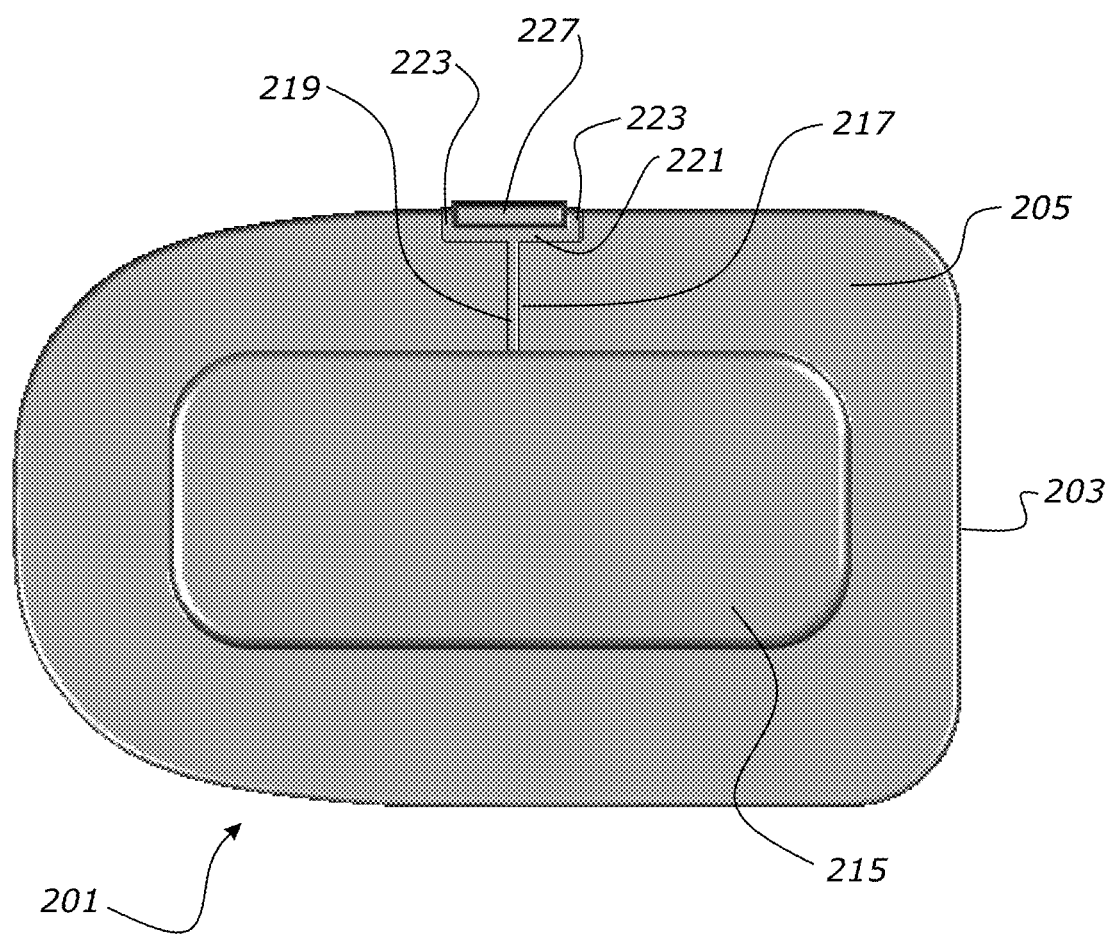
FIG. 17 is a top plan view of the stand.
Figure 18:
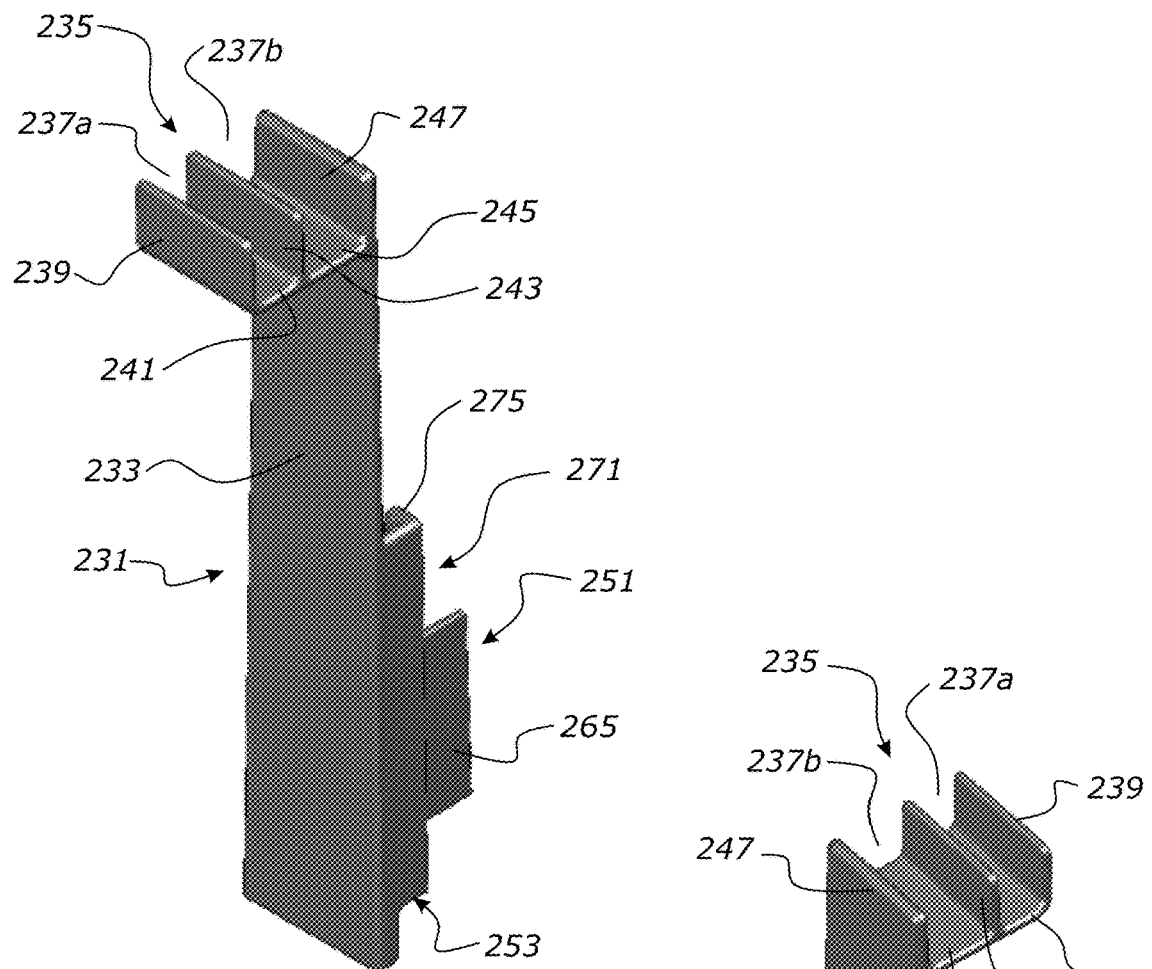
FIG. 18 is a left/front overhead perspective view of a conduit and/or patient interface holder of the support assembly.

The upper surface 205 of the base 203 may have an optional alignment feature 217 as shown in FIGS. 12, 13, and 17 to assist with aligning the holder 231 with the stand 201. In the form shown, the alignment feature comprises an indented region that has a general T-shape. The indented region comprises a base portion 219 that extends from the recess 215 towards a periphery of the base, a transversely extending portion 221 located adjacent the periphery of the base, and two shortened extensions 223 that extend from the transverse portion 221 to the periphery of the base. The alignment feature 217 could have a different configuration. The alignment feature 217 may have the same depth as the recess 215 or may have a different depth.

The stand 201 is configured to support the holder 231 in an upstanding configuration from the base. An upstand spigot 225 extends upwardly from a periphery of the base 203 to releasably mount the base 203 of the stand to the holder 231. The upstand 225 has a tapered configuration in which the dimensions of the upper end of the upstand 225 are smaller than the dimensions of the lower end of the upstand. The upstand terminates at a top edge 227. The tapering of the upstand 225 makes the shape easier to mould and improves assembly as mating occurs only at the end of travel of the upstand into the lower mount 253 of the holder 231. Engagement of the lower mount 253 with the upstand 225 is described in more detail below.

The upstand 225 could alternatively be a different shape. Exemplary configurations are shown in side view in FIGS. 27a to 27f. For example, the upstand could be a straight non-tapered configuration such as a rectangular or square configuration as shown in FIG. 27b. Such a configuration may require greater force to engage and disengage the holder 231 to/from the upstand 225 due to the increased interaction between the surfaces of the parts.

Figure 27A:
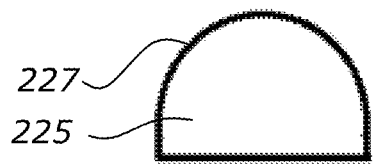
FIGS. 27a to 27f schematically show side views of alternative exemplary shapes for the upstand of the base.
Figure 27B:
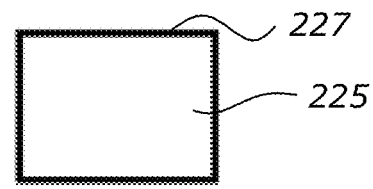
Figure 27C:
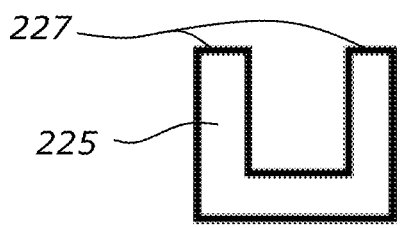
Figure 27D:
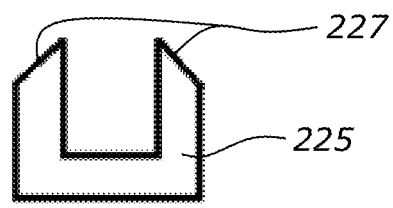
Figure 27E:
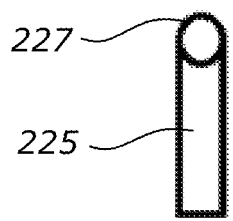
Figure 27F:
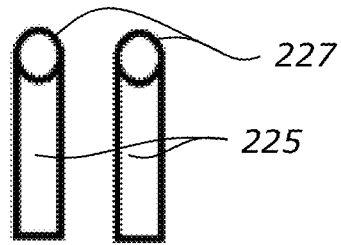

Other exemplary shapes for the upstand 225 include a bulbous configuration with an arcuate or semi-circular upper wall 227 as shown in FIG. 27a, a substantially U-shaped configuration with upper walls 227 that are substantially perpendicular to elongate direction of the uprights of the U as shown in FIG. 27c, a substantially U-shaped configuration with upper walls 227 that are tapered or angled relative to the elongate direction of the uprights of the U as shown in FIG. 27d, a narrower elongate upright with an arcuate or semi-circular upper wall 227 as shown in FIG. 27e, or a pair of spaced apart uprights as shown in FIG. 27f which may each, for example, have the configuration corresponding to FIG. 27e or a different configuration. Other suitable shapes could also be used.

The shape of the lower mount 253 may be as described below or could be a different shape that is complementary to any of the upstand 225 shapes.

The upstand 225 is located at the periphery of the base 203 between the transversely extending portion 221 and shortened extensions 223 of the alignment recess.

Referring to FIGS. 18 to 24, the holder 231 for the conduit and/or patient interface such as a cannula comprises an elongate upstanding component comprising an upstand arm 233. A holder portion 235 is positioned at or adjacent and at the end of the arm 233 and extends outwardly from one side of the arm. A dual mount 251 is positioned at or toward an opposite lower end of the arm 233 and extends from the opposite side of the arm from the holder portion 235. Having the holder portion 235 extending from an opposite side of the arm from the mount 251 is beneficial, as the holder portion will not interfere with the apparatus 10 being inserted into or removed from the mount 251. However, the holder portion 235 and the mount 251 may be provided on the same side of the arm 233 if the arm 233 is sufficiently long to avoid that interference. The dual mount 251 is arranged to releasably couple the holder 231 to the stand 201 and to releasably couple the holder 231 to the breathing assistance apparatus 10.

The holder portion 235 comprises at least one mechanical feature for holding a conduit and/or patient interface such as a cannula of the breathing assistance apparatus 10 in place relative to the support assembly 200 and relative to the breathing assistance apparatus 10 when the breathing assistance apparatus is supported by the support assembly 200. In the form shown, the holder portion comprises an outer mechanical feature 237a and an inner mechanical feature 237b, with one of the mechanical features being configured to support the conduit 16 and the other of the mechanical features being configured to support the patient interface such as a cannula 17.

The outer mechanical feature 237a comprises a recess defined by an outer wall 239, a base wall 241, and an intermediate wall 243. The inner mechanical feature 237b comprises a recess defined by the intermediate wall 243, a base wall 245 that is contiguous with the base wall 241, and an inner wall 247 that is contiguous with the arm 233. The inner mechanical feature 237b is larger than the outer mechanical feature 237a, so that the larger and heavier accessory is supported closer to the arm 233. In different configurations, the mechanical features could be the same size or the outer mechanical feature could be larger than the inner mechanical feature.

The holder portion 235 could comprise one, two, three, or more mechanical features.

The mechanical feature(s) has/have a shape that is complementary to the shape of the conduit and/or patient interface such as a cannula to be held by the mechanical feature(s). The mechanical feature(s) could have any suitable configuration. For example, the mechanical feature(s) could comprise one or more of: a recess or groove; a clip; a hinge mechanism; a compliant sling or strap; a hook and loop fastener; or any other suitable configuration. In one configuration, the mechanical features comprise two recesses, with one of the recesses configured to receive the conduit and the other of the recesses configured to receive the patient interface such as a cannula. In another configuration, the mechanical feature(s) comprise(s) one or more compliant slings. In another configuration, the mechanical feature(s) comprise(s) one or more clips. In another configuration, the mechanical feature(s) comprise(s) one or more hook and loop fasteners that is/are configured to secure around the conduit and/or patient interface such as a cannula to hold the conduit and/or patient interface such as a cannula in position.

When the holder has a plurality of mechanical features, different mechanical features could be used in combination in the holder portion 235.

The dual mount 251 comprises a lower mount 253 and an upper mount 271.

Figure 24:
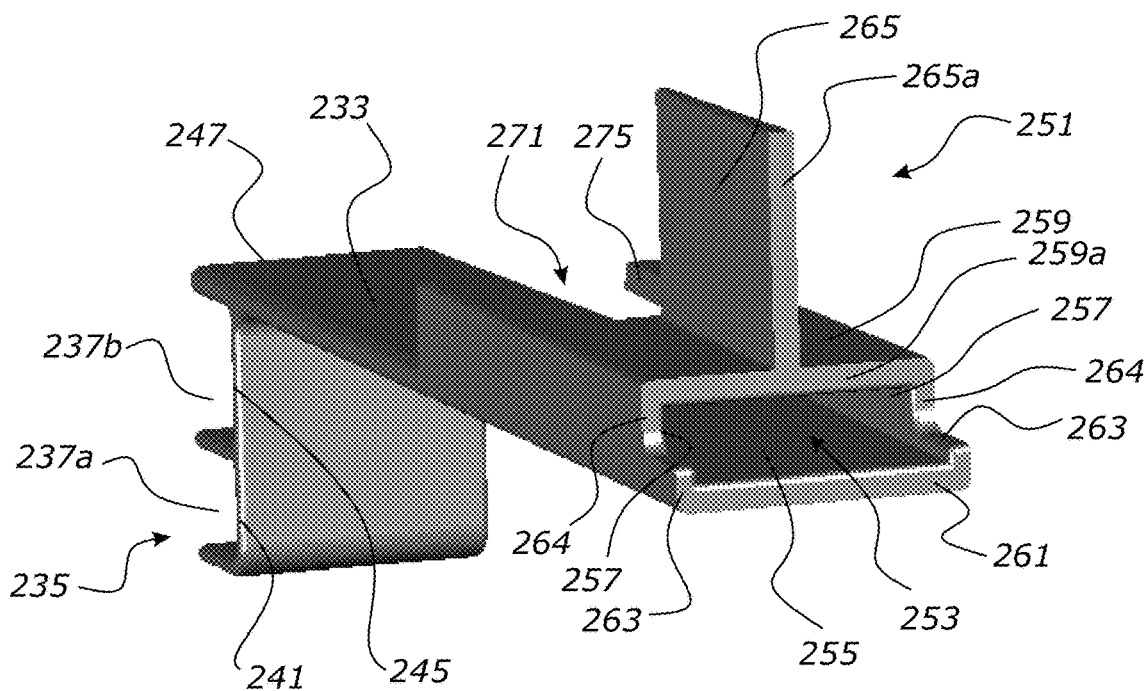
FIG. 24 as in underside perspective view of the holder showing a mount to mount the holder to the stand.

The lower mount 253 is arranged to releasably mount the holder 231 to the upstand 225 of the stand 201. Referring to FIG. 24 in particular, the lower mount comprises a receptacle to receive the upstand 225. The receptacle is defined by a wall 255 that is contiguous with the arm 233, a pair of spaced apart side walls 257, and an opposed wall 259. The receptacle has a shape that is complementary to the shape of the upstand 225. In one configuration, the interior of the receptacle has a tapered shape corresponding substantially to the tapered shape of the upstand, such that the lower mount 253 and the upstand 225 will releasably lock with a taper lock when the upstand 225 is engaged in the lower mount 253. Alternatively, the receptacle may have a shape that differs from the tapered shape of the upstand 225, but surfaces of the upstand will engage with opposed walls of the receptacle to lock the component together. The tapered configuration may provide an insertion depth limitation of the upstand 225 into the receptacle. In either configuration, the engagement will be sufficient that the support assembly 200 can be lifted by the holder 231 without the holder 231 disconnecting from the stand 201.

The receptacle may comprise a stop to prevent overinsertion of the upstand 225 into the receptacle. For example, the stop may comprise a projection or protrusion, or any other suitable configuration. The stop may be provided by an upper wall of the receptacle.

Figure 11:
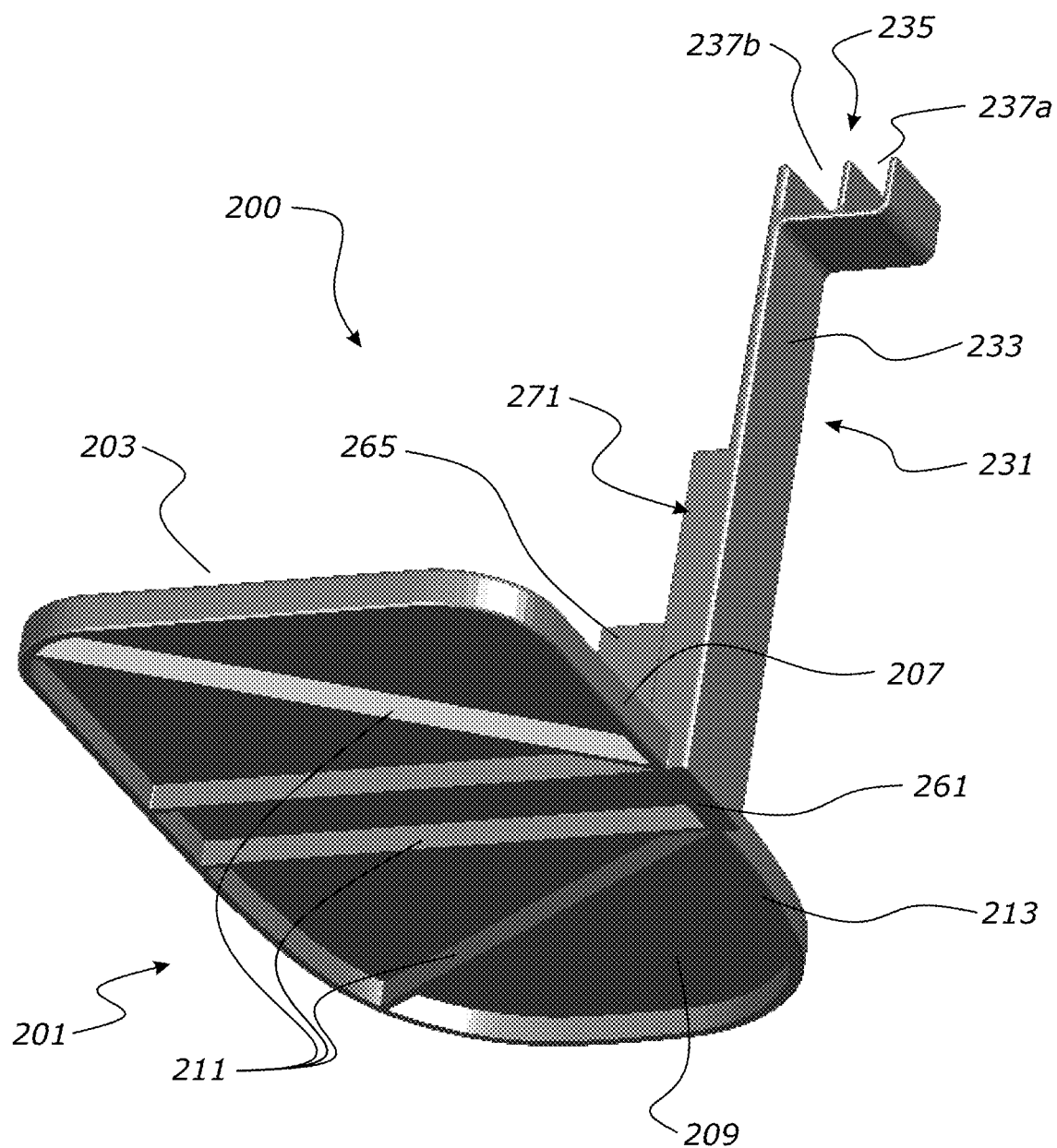
FIG. 11 is a rear/left underside perspective view of the support assembly.

A portion of the wall 255 extends further downwardly than the wall 259, such that when the holder 231 is mounted to the stand 201, a bottom edge 261 of the wall 255 sits flush with the bottom edge 213 of the peripheral wall 207 of the base, as shown in FIG. 11. That enables the bottom edge 261 of the wall 255 to also contact the support surface to provide additional stability to the holder 231.

A pair of relatively shallow side walls 263 extend inwardly from the extended portion of the wall 255 and rest against the peripheral wall 207 of the base 203. Referring to FIGS. 13 and 24, lower edges 264 of side walls 257 have a shape that is complementary to the shape of the two shortened extensions 223 of the alignment feature, and are received in the two shortened extensions 223 when the holder 231 is mounted to the stand 201. A lower edge 259a of the wall 259 has a shape that is complementary to the shape of the transverse portion 221 of the alignment feature, and is received in the transverse portion 221 when the holder 231 is mounted to the stand 201.

A projecting rib 265 extends inwardly from the wall 259 of the lower mount. A lower edge 265a of the rib has a shape that is complementary to the shape of the base portion 219 of the alignment feature, and is received in the base portion 219 when the holder 231 is mounted to the stand 201.

The alignment feature assists with aligning the holder 231 with the stand 201 as the upstand 225 is inserted into the lower mount 253, and with preventing rotation of the holder 231 relative to the stand 201 once the holder 231 is mounted to the stand 201. The rib 265 also assists with preventing inward tilting of the holder 231 toward the centre of the stand under loading, improving the stability of the holder.

The lower mount 253 and stand 201 may have different configurations while still providing for releasable coupling of the lower mount 253 and the stand 201. For example, rather than the upstand 225 being configured to be received in the receptacle of the mount 253, the upstand 225 may be configured to receive part of the mount 253. Alternative configurations may be used, such as adhesive, a hook and loop fastener, a clip, a ridge and groove mechanism, or other releasable connection for example.

The lower mount 253 may be integral with the holder 231 or may be separately formed and coupled to the holder 231.

The releasable configuration of the holder 231 and the stand 201 allows for easy dismantling and/or transport.

Figure 19:
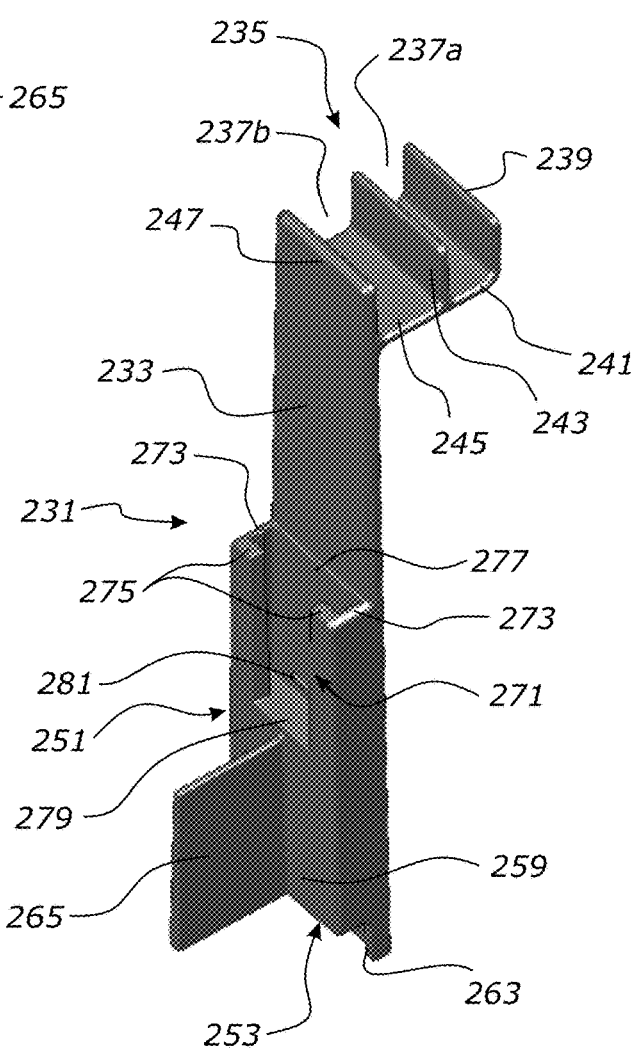
FIG. 19 is a right/rear overhead perspective view of the holder.
Figure 23:
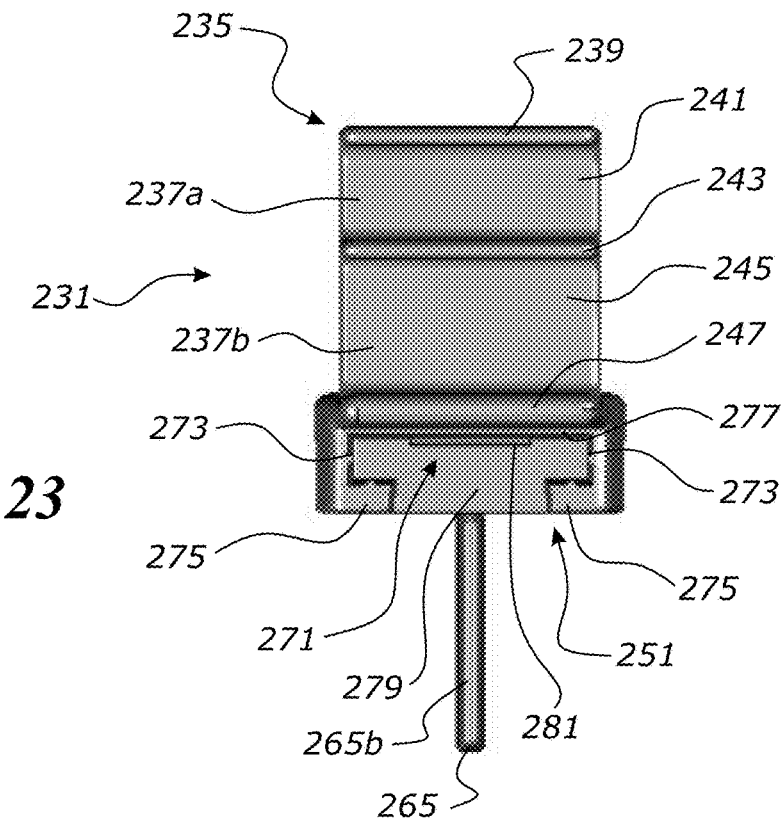
FIG. 23 is an overhead plan view of the holder.

The upper mount 271 is arranged to releasably mount the holder 231 to the breathing assistance apparatus 10. Referring to FIGS. 19 and 23, the upper mount 271 comprises a receptacle having opposed slots formed by side walls 273, relatively narrow front walls 275, and a rear wall 277 that extends between the side walls. The rear wall 277 is wider than the front walls 275, so that the front walls define an opening between the slots. The base of the receptacle is defined by a bottom wall 279.

In the form shown, the upper mount 271 and the lower mount 253 are positioned immediately adjacent each other so that a single wall 279 can form the base of the receptacle of the upper mount 271 and the top of the receptacle of the lower mount 253. In alternative configurations, the upper and lower mounts may be spaced further apart, and may have separate walls forming the base of the receptacle of the upper mount and the top of the receptacle of the lower mount.

The receptacle of the upper mount 271 is arranged to receive the tongue 131 of the mount 127 of the apparatus 10, by sliding the tongue downwardly into the slots of the upper mount with the edges of the tongue received between the shortened front walls 275 and the rear wall 277. The slots and the side walls 273 of the receptacle form alignment features to align the upper mount 271 with the complementary mount 127 of the breathing assistance apparatus. In alternative configurations, different alignment feature(s) may be used, such as one or more ribs, protrusions, and/or other features. The alignment feature(s) protect against horizontal movement or misalignment of the support assembly 200 with the apparatus 10 and assist with controlling the insertion extent of the tongue 131 of the apparatus into the receptacle. Additionally, or alternatively, one or more stops may be provided to limit the insertion extent of the tongue 131 into the receptacle.

The upper mount 271 further comprises a connection feature to releasably fasten the support assembly 200 to the breathing assistance apparatus 10. In the form shown, a protrusion in the form of a transverse bump 281 projects into the receptacle of the mount from the wall 277. The bump 281 is configured to engage with the bump 133 on the tongue 131 of the apparatus 10. As the tongue 131 is inserted into the receptacle of the upper mount 271, the tongue 131 will resiliently flex so that the bump 281 can pass bump 133. The protrusions could have different configurations, and could be positioned on different surfaces of the mount and tongue.

Figure 25:
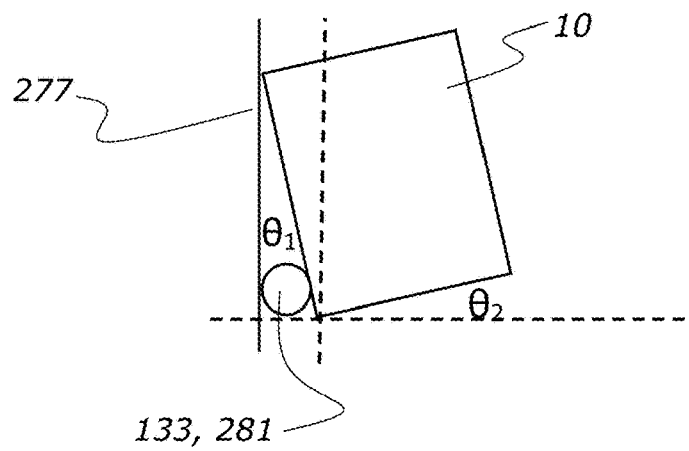
FIG. 25 is a schematic view showing exemplary angles of the housing of the apparatus when mounted to the support assembly.

As shown in FIG. 25, when the apparatus 10 is mounted to the support assembly 200, the bump 133 causes the apparatus to lean towards the wall 277 of the support assembly. Without the bump, a user may perceive the apparatus leaning away from the stand (due to the base of the apparatus swinging in towards the stand) and be concerned that the apparatus is not securely held. The bump 133 therefore positions the apparatus such that it leans inwardly towards the stand so that a user is unlikely to be concerned regarding the coupling between the stand and the apparatus.

The bump 133 may be configured to cause the unit apparatus to lean in towards the stand by any suitable angle. For example, angle $\theta_1$ may be approximately 1-15°, or approximately 1-10°, or approximately 1-7°, or approximately 1-5°, or approximately 1-2°. Therefore $\theta_2$ is $\geq 0°$.

The mounting will be sufficient that the apparatus 10 is securely held with a reasonable buffer strength to hold the apparatus through likely usage cases (e.g. a user leaning on the apparatus, accidental bumping of the apparatus), whether or not the bump is present. The bump addresses the visual look and user's perception of the case. The mounting will be sufficient that if the user lifts the apparatus 10 with normal force (for example to lift the apparatus off the floor), the apparatus 10 will not disconnect from the support assembly.

Due to the resilient nature of the tongue, if the user wants to disconnect the apparatus 10 from the support assembly (for example, to put the apparatus 10 in a storage case), they can achieve that by applying sufficiently large upward force to the apparatus 10 and downward force to the support assembly 200.

The position of the upper mount 271 on the holder 231 is such that an underside 115 of the breathing assistance apparatus 10 will be positioned with a spacing above a top surface 205, 215 of the base 203 of the stand 201, when the breathing assistance apparatus 10 is coupled with the support assembly 200. The spacing between the top surface 205, 215 of the base and the underside 115 of the breathing assistance apparatus will advantageously be sufficient to provide a storage space for accessories of the breathing assistance apparatus when they are not in use. For example, a liquid bag and tubes for delivering liquid to the liquid chamber 500, breathing conduit, and/or the power cord of the apparatus.

In some configurations, the spacing between the upper surface of the receptacle 215 and the underside 115 of the breathing assistance apparatus 10 may be between about 50 mm and about 150 mm, or may be between about 50 mm and about 100 mm, or may be between about 70 mm and about 90 mm, or may be about 80 mm, for example. If a receptacle 215 is not provided, that may be the spacing between the upper surface 205 of the base and the underside 115 of the apparatus 10.

Figure 4:
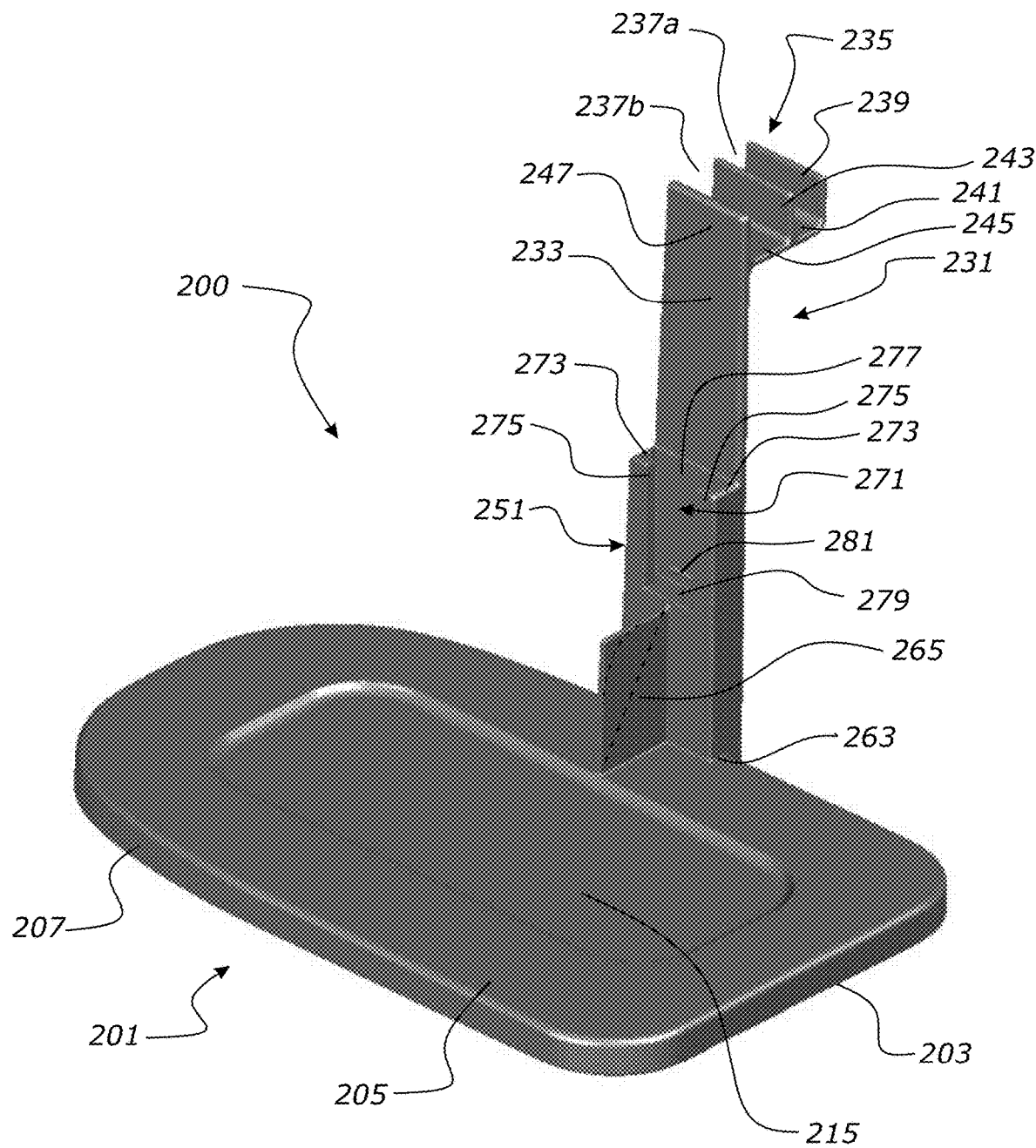
FIG. 4 is a right/rear overhead perspective view showing a support assembly for the breathing assistance apparatus and/or a conduit and/or patient interface such as a cannula.
Figure 5:
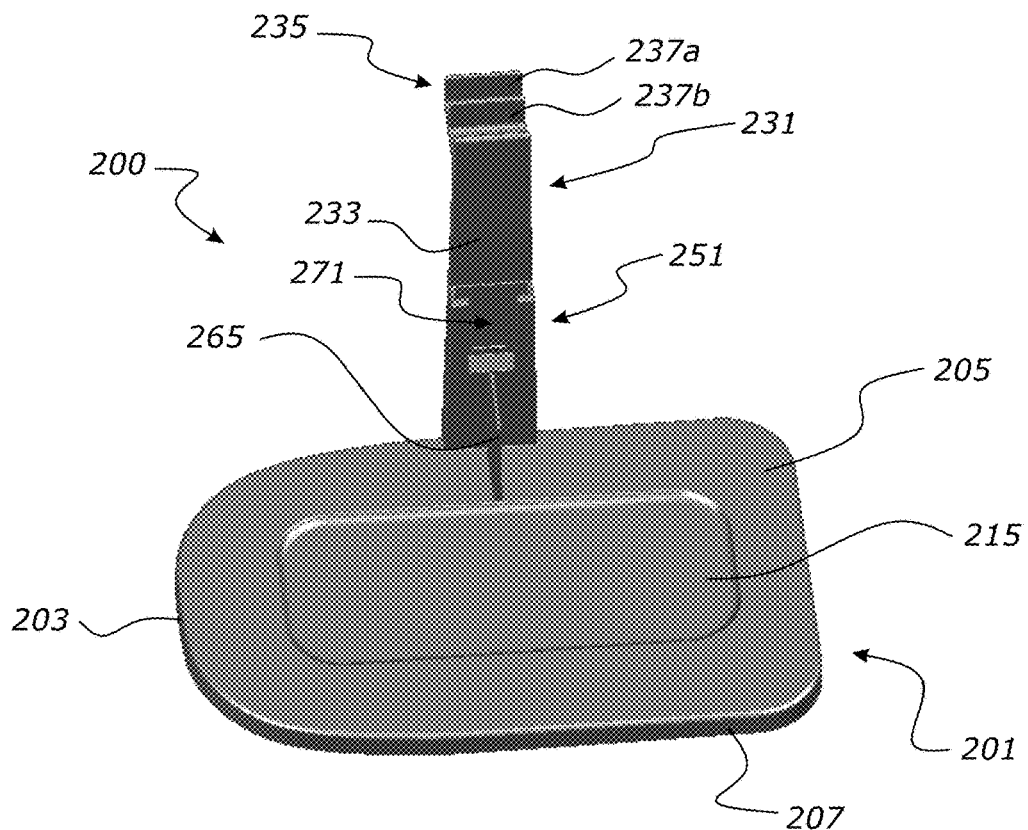
FIG. 5 as a right side overhead perspective view showing the support assembly.
Figure 6:
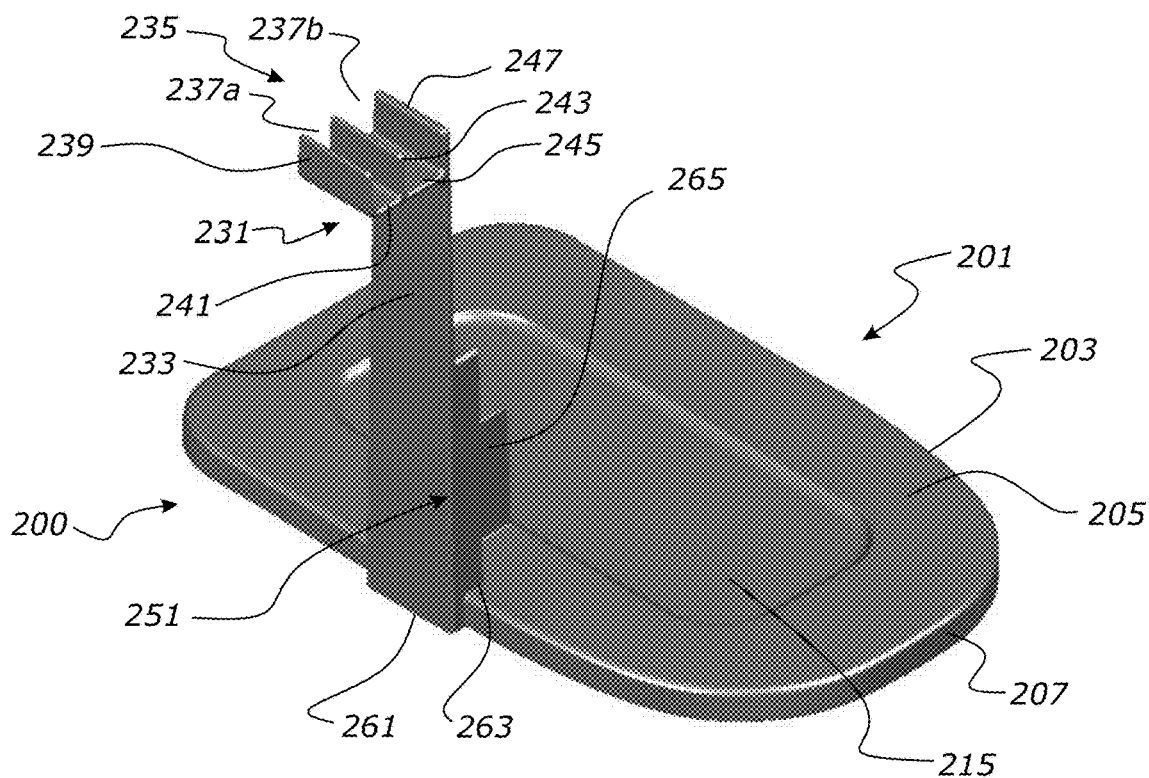
FIG. 6 is a left/front overhead perspective view of the support assembly.
Figure 7:
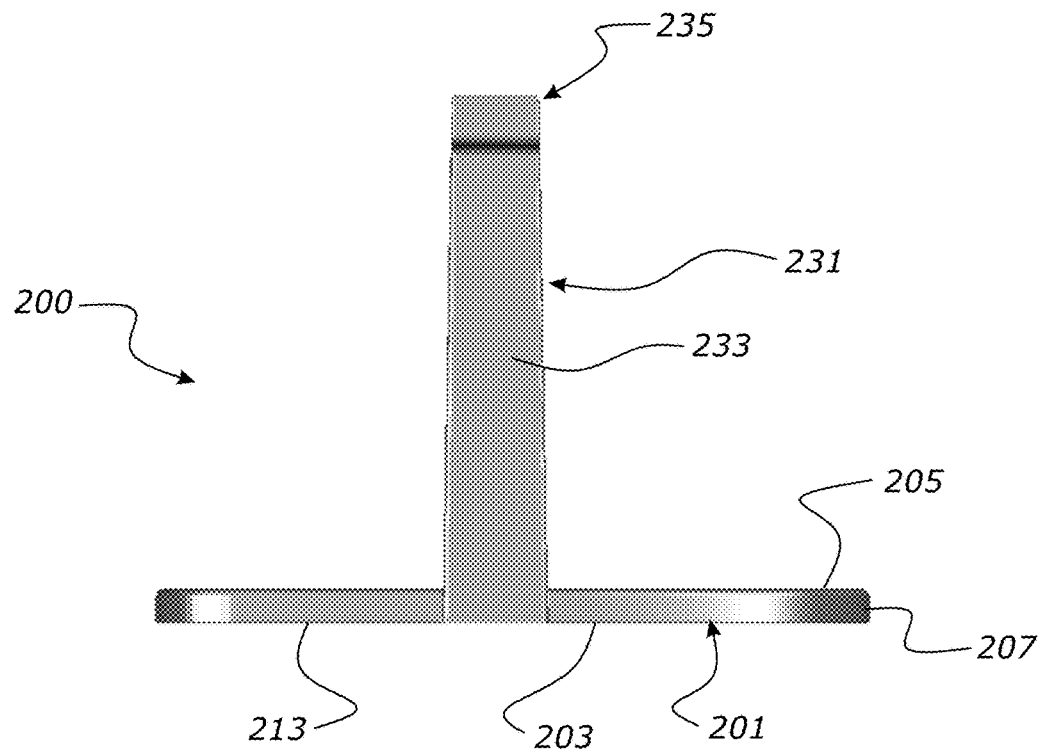
FIG. 7 is a left side view of the support assembly.
Figure 8:
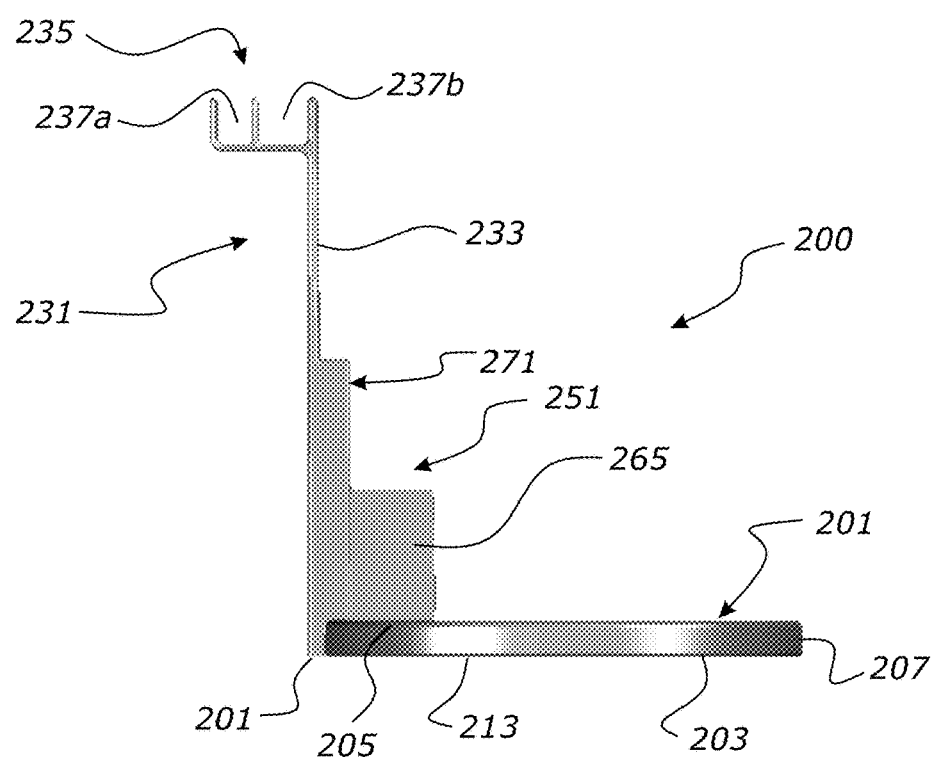
FIG. 8 is a front view of the support assembly.
Figure 9:
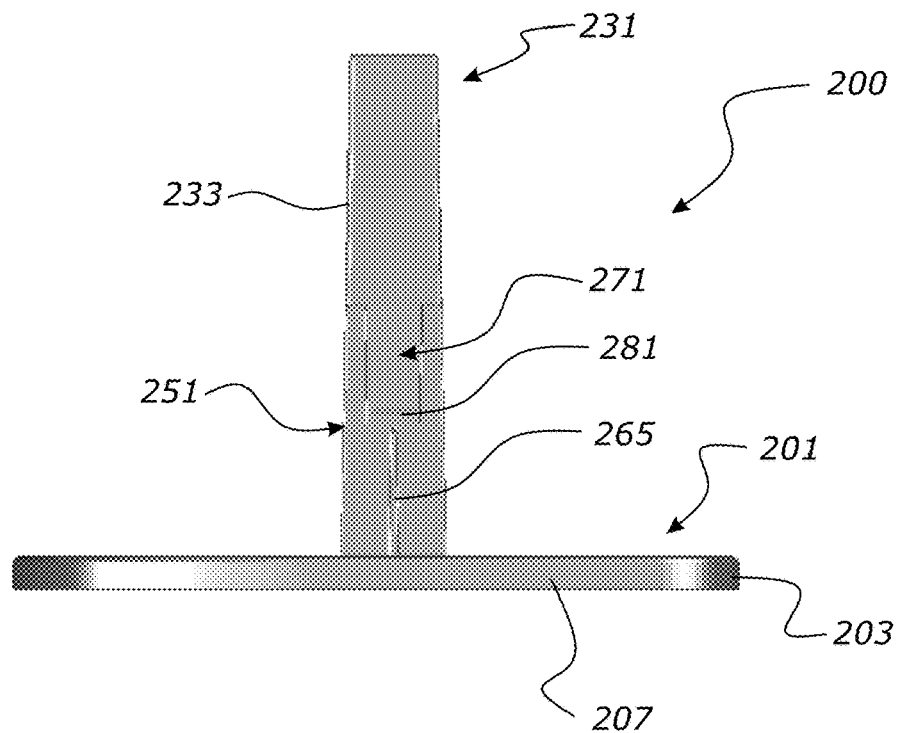
FIG. 9 is a right side view of the support assembly.
Figure 10:
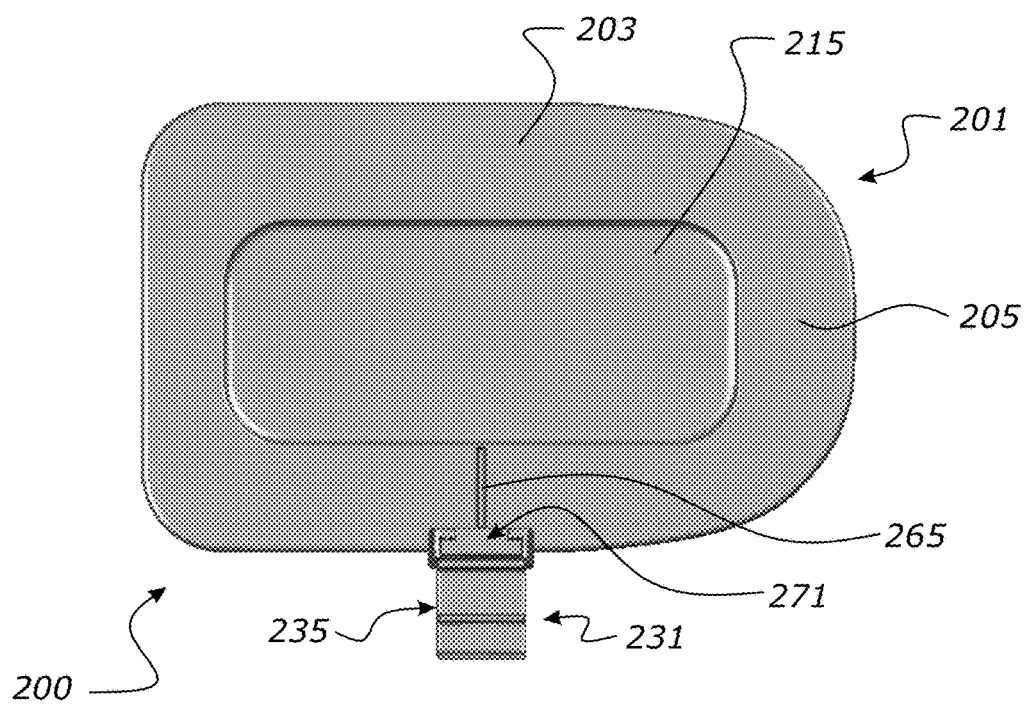
FIG. 10 is a top plan view of the support assembly.
Figure 28:
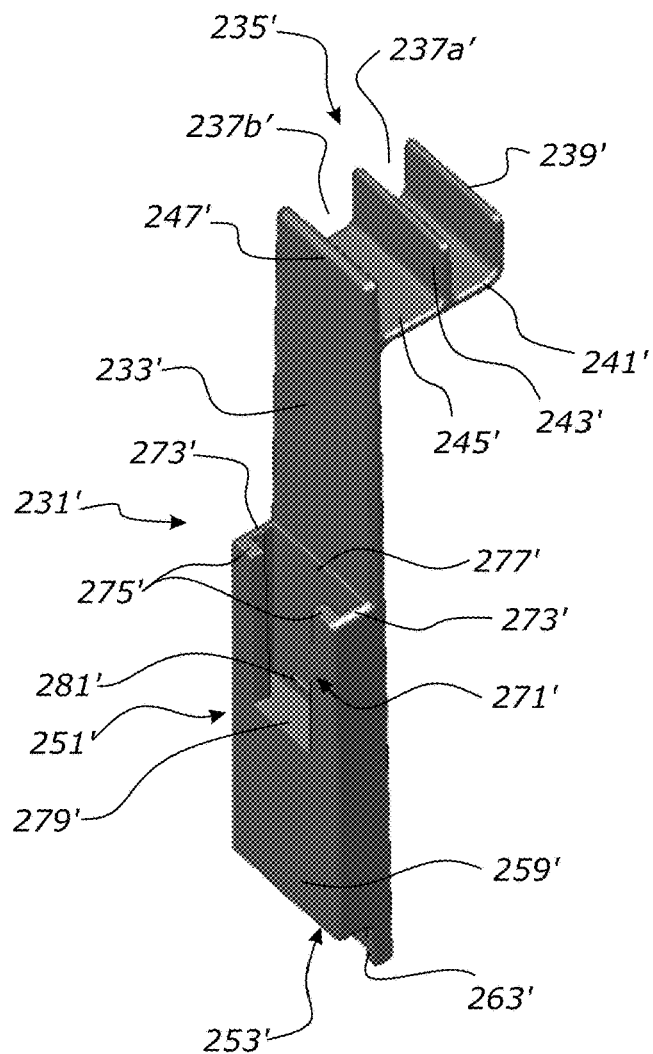
FIG. 28 is a right/rear overhead perspective view of an alternative configuration conduit and/or patient interface holder of the support assembly.

The rib 265 on the holder 231 may also support the underside 115 of the apparatus 10, to assist with holding the apparatus with the spacing above the base 203. For example, the top surface 265b of the rib 265 may contact the underside 115 of the apparatus 10. Alternatively, the apparatus 10 may be held solely by the upper mount 251. In such a configuration, the rib 265 may not be provided, or may have a different shape such as having a curved or angled upper edge as shown in FIG. 4 for example. FIG. 28 shows an alternative configuration holder 231' that does not have a rib. The features and functionality are otherwise the same as described above, and like reference numerals indicate like parts with the addition of a prime (').

The upper portion of the upstand arm 233 is configured to be spaced apart from the side wall 109 of the housing of the breathing assistance apparatus 10 when the apparatus 10 is coupled with the upper mount 271. Due to the spacing between the upper portion of the upstand arm 233 (which may be straight) and the side wall 109, the upper portion of the upstand arm 233 thereby has a hook-like configuration, which enables a power cord of the apparatus 10 to be wrapped around that upper portion of the arm 233 between the upper and the breathing assistance apparatus 10, to store the power cord when the apparatus 10 is not in use. Additionally or alternatively, the holder 231 may be provided with one or more dedicated features for that purpose, such as hook(s), clip(s), protrusion(s), or a curved portion added to the holder 231.

The holder 231 is upstanding and is configured such that the mechanical feature(s) 237a, 237b is/are located higher than the breathing assistance apparatus 10 or at or adjacent to breathing assistance apparatus 10, when the upper mount 271 is coupled with the breathing assistance apparatus 10. Thereby, the conduit and/or patient interface such as a cannula is/are held above the breathing assistance apparatus 10 or at or adjacent a top of the breathing assistance apparatus 10, when the upper mount 271 is coupled with a breathing assistance apparatus and the conduit and/or patient interface such as a cannula is/are held by the mechanical feature(s). That means that the conduit and/or patient interface such as a cannula will be easily accessible by a user when they wish to use the apparatus, even if the support assembly 200 is positioned on the floor. Holding the conduit and/or patient interface such as a cannula off the floor is likely to reduce the likelihood of the conduit and/or patient interface such as a cannula getting contaminated or dirty, which is particularly useful in a home environment where a user is likely to reuse those accessories. There are possible benefits relating to condensate drainage back to the liquid chamber 500/ambient environment if the holder 231 holds the conduit and/or patient interface such as a cannula higher than the main housing 100 of the apparatus 10. Because the holder 231 provides storage for the conduit and/or patient interface such as a cannula, the used patient interface such as a cannula does not need to be placed on a bedside table after use, but can instead be supported by the holder 231. Additionally or alternatively, the used patient interface such as a cannula could be positioned in the space between the underside 115 of the breathing assistance apparatus 10 and the top surface 205, 215 of the base 203.

The support assembly 200 will typically be provided or used in combination with a breathing assistance apparatus 10 having a conduit 16 and/or patient interface such as a cannula 17. The support assembly may be provided as an aftermarket component.

Figure 26:
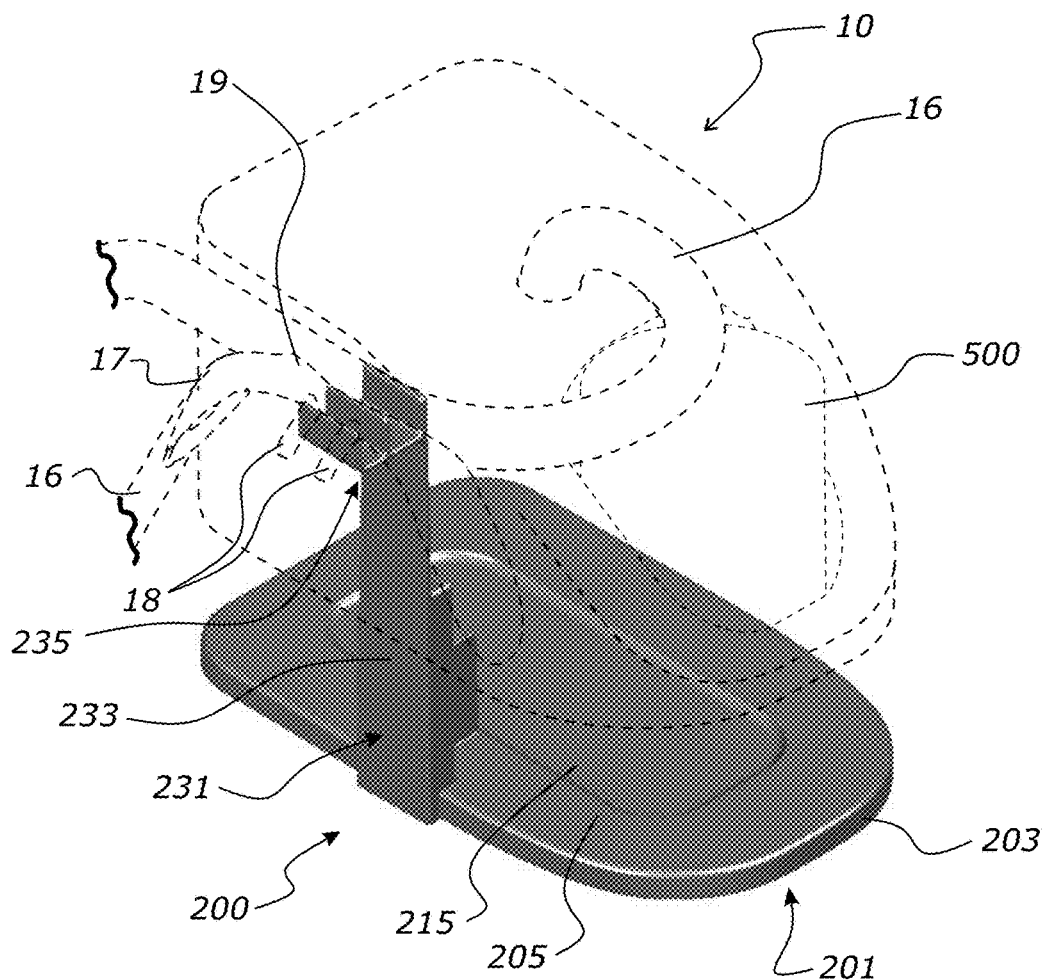
FIG. 26 is a perspective view showing the breathing assistance apparatus, patient conduit, and patient interface such as a cannula being supported by the support assembly.

The apparatus 10 can be coupled with the support assembly 200 which will be positioned on a support surface, either when the apparatus 10 is in use or is not in use. When the apparatus 10 is not in use, the conduit 16 and/or patient interface such as a cannula 17 will be held in place relative to the support assembly 200 and the apparatus 10, and held above the support surface, by the mechanical feature(s) 237a, 237b, as shown in FIG. 26 for example.

The support assembly 200 provides a portable arrangement that is easily placed on a support surface such as floor or table, and that keeps the conduit and/or patient interface such as a cannula and apparatus 10 off the ground.

The holder 231 may be used without the stand 201. With the holder 231 coupled to the apparatus 10, but with no stand 201, the holder holds the conduit and/or patient interface such as a cannula in a raised position off the support surface, but does not raise the apparatus 10 off the support surface. The mounting between the holder 231 and the apparatus 10 will support the upstand arm in an upright configuration from the apparatus 10. By combining the holder 231 and the stand 201 so that the apparatus 10 is raised, a larger battery 125 may be used in the apparatus 10 because the battery can project downwardly beyond the underside 115 of the apparatus 10 without requiring the apparatus to be tilted on the support surface. A larger battery may typically have greater capacity, allowing the device 10 to be used on battery power for longer.

When the power cord is plugged into the apparatus, the power cord can be downwardly vertically extending to reduce the horizontal footprint of the apparatus and to provide a large bend radius on the cord. By having the apparatus 10 raised off the support surface, the power cord can be easily stored in the space between the stand 201 of the holder 231 and the apparatus 10 even if the power cord is plugged into the apparatus. Alternatively, the power cord could be stored in the space between the stand 201 of the holder 231 and the apparatus 10 when the power cord is unplugged from the apparatus.

The support assembly 200 can be made from any suitable material, such as injection moulded plastic for example.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Features from any of the described embodiments may be combined with each other and/or an apparatus may comprise one, more, or all of the features of the above described embodiments. Moreover, not all of the features, aspects and advantages are necessarily required to practice the present disclosure. Accordingly, the scope of the present disclosure is intended to be defined only by the claims that follow.

The various configurations described are exemplary configurations only. Any one or more features from any of the configurations may be used in combination with any one or more features from any of the other configurations.

For example, the support assembly 200 is described as having both a holder 231 and a stand 201 that can be releasably coupled together. In an alternative configuration, the holder and stand may be integrally formed, and the upstand 225 and lower mount 253 may not be provided.

Figure 29:
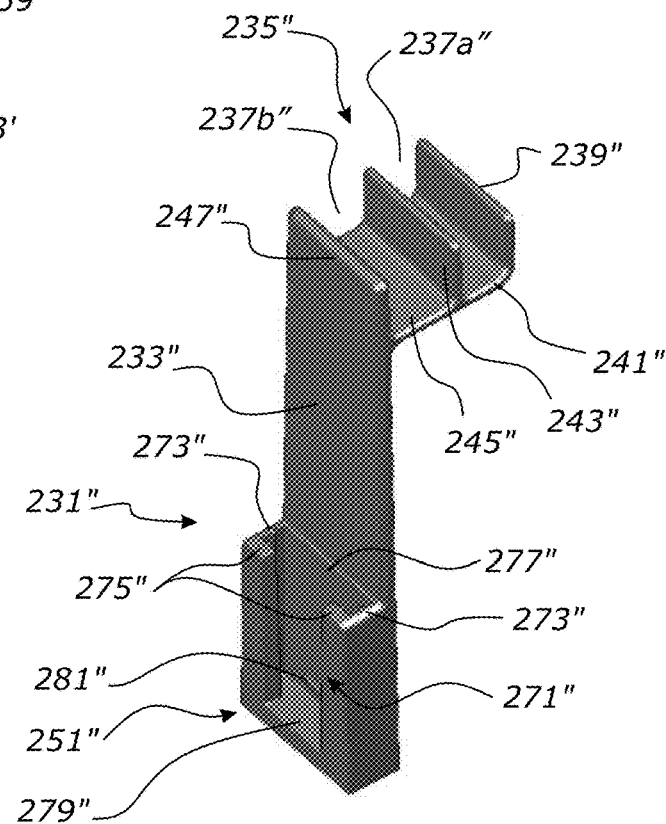
FIG. 29 is a right/rear overhead perspective view of an alternative configuration conduit and/or patient interface holder of the support assembly.

As another example, while the support assembly or apparatus 200 is described as having both a holder 231 and a stand 201, different configurations of the apparatus may not have both features. For example, in some configurations, the apparatus 200 may only comprise a holder 231 having a mount 271 for releasably mounting the holder 231 to the breathing assistance apparatus 10. FIG. 29 shows such a configuration. In this configuration, the holder 231" does not have a lower mount for mounting to a stand 201 but is provided with just the upper mount 271". The holder 231" does not project any significant distance below the mount 271" so that the bottom of the holder 231" does not project beyond the underside 115 of the apparatus 10, and therefore does not interfere with the apparatus 10 sitting flat on a support surface. The features and functionality are otherwise the same as described above for holder 231, and like reference numerals indicate like parts with the addition of a double prime ("). In some other configurations, the apparatus 200 may only comprise a stand 201 and a mount 271 for releasably mounting the stand 201 to the breathing assistance apparatus 10 with a spacing above the stand 201. The configurations shown in FIGS. 18 to 24 and FIG. 28 could be releasably mounted to the apparatus 10 to act as a holder, without using the stand 201.

In another example, the support apparatus 200 may not be configured to hold the breathing assistance apparatus with a spacing between the underside 115 of the breathing assistance apparatus 10 and the upper surface 205, 215 of the base 203. In an alternative configuration, the mount 271 may be positioned so that when the apparatus 10 is engaged with the mount, there may be substantially no gap between the base 203 and the underside of the apparatus 115.

In another alternative configuration, the breathing assistance apparatus may be positioned on, and be supported by, the base 203. In such a configuration, the base 203 and the housing of the breathing assistance apparatus will be provided with complementary engagement features to locate the apparatus on the base. FIG. 3 shows an exemplary configuration of recesses 143 in the underside 115 of the apparatus 10 to engage with engagement pins (not shown) on an upper surface of the base. The recesses may be provided by apertures that receive fasteners to couple the upper and lower housing parts 102, 104 together. The fasteners could insert into the screw recesses on the underside of the lower chassis part, or could protrude through the recesses into the upper chassis part to join the upper and lower chassis parts together. The number and/or configuration of engagement features may vary. The support apparatus 200 may be provided with both the mount 271 and the engagement features. When a user wants to transport the apparatus 10, they can disconnect the holder 231 from the apparatus 10 and from the stand 201, and can locate the apparatus 10 directly in position on the base 203 using the engagement features to make the device more compact. The pins and recesses may be configured so that they are aligned when the apparatus 10 is positioned directly on the base 203 (whether or not the holder 231 is coupled to the stand 201), but so that they are misaligned when the apparatus 10 is engaged with the mount 271. When the pins and recesses are aligned, the device and stand can pack down to a small size for transportation. When the apparatus 10 is engaged with the mount 271 and the pins and recesses are misaligned, the pins may engage the underside 115 of the apparatus to assist with supporting the apparatus 10 on the support assembly 200. The pins and recesses (or other complementary engagement features) may be provided in combination with, or instead of the rib 265.

The mount 271 may be provided as part of the holder 231, the base 203 (e.g. on the upstand 225), or both the holder 231 and the base 203. The mount 271 may be integrally formed with the holder 231 and/or base 203, or may be formed separately but coupled to the holder 231 and/or base 203.

As another example, while the support assembly 200 is described as engaging with the side of the housing of the breathing assistance apparatus 10, the support assembly could engage with any suitable part of the housing, such as an upper part, lower part, side part, front part, or rear part.

In another example, the support assembly could have a mechanical feature designed for holding a liquid bag above the flow therapy apparatus 10. The liquid bag could supply liquid to a liquid chamber 300 of the flow therapy apparatus 10, as described above. This would be beneficial in situations where the supplying the liquid chamber 500 with liquid from the liquid bag requires the liquid bag to be vertically higher than the liquid chamber 500. Allowing for a liquid bag to be used to supply the liquid chamber 500 would increase the volume of liquid available and reduce the frequency with which the user would need to refill the liquid chamber 500.

Figure 30:
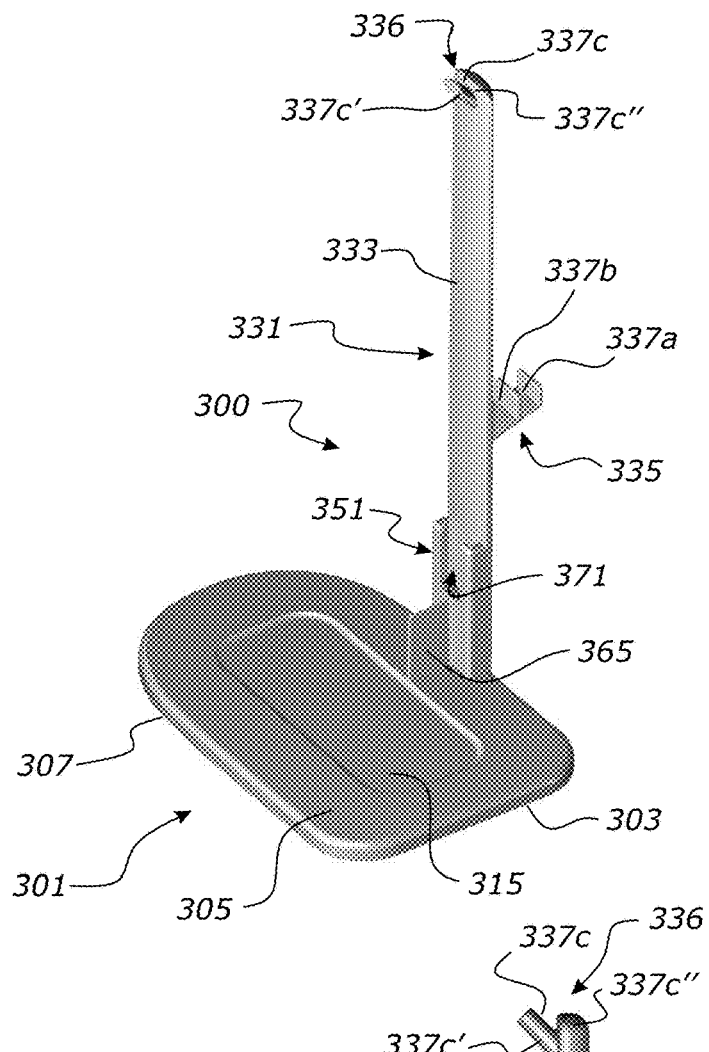
FIG. 30 is a right/rear overhead perspective view showing an alternative configuration support assembly for the breathing assistance apparatus and/or a conduit and/or patient interface such as a cannula.

FIG. 30 shows such an exemplary configuration of a support apparatus comprising a support assembly 300 having a mechanical feature 337c for holding a liquid bag. Unless described below, the features and functionality are otherwise the same as described above for support assembly 200, and like reference numerals indicate like parts with the addition of 100. As can be seen from the sizes of components in FIG. 30 compared to the sizes of components in FIG. 4, the upstand arm 333 is longer in this configuration compared to upstand arm 233. The upstand arm 333 of the holder 331 has a conduit and/or patient interface such as a cannula holder portion 335 and a liquid bag holder portion 336. In the form shown, the liquid bag holder portion 336 comprises a mechanical feature 337c for holding the liquid bag. The mechanical feature 337c is positioned at or adjacent the upper end of the upstand arm 333, and comprises a recess that is formed between a cantilevered member 337c' that extends transversely outwardly and upwardly from the upstand arm 333, and an upper portion 337c" of the upstand arm 333. The cantilevered member may be configured to be inserted into a loop or aperture in the liquid bag (not shown) to hang the liquid bag from the upstand arm 333. The mechanical feature could be any other suitable shape, such as upwardly-opening U-shaped member, or any of the other configurations described in the specification for the mechanical features for supporting the conduit and/or patient interface such as a cannula, for example.

Rather than being part of the holder 331, the mechanical feature 337c for holding the liquid bag could be a holder that is separate from the holder 331; for example, a separate upstanding arm that is integrally formed as part of, or is mountable to, the stand 301. When the two holders are separate, the holder for the liquid bag could be configured so that the mechanical feature 337c is located at the same height, higher, or lower than the mechanical features 337a, 337b for holding the conduit and/or patient interface such as a cannula. Ideally, the mechanical feature 337c for holding the liquid bag would be vertically higher than the mechanical feature(s) 337a, 337b so that the liquid bag can be positioned high enough for the liquid bag to adequately deliver liquid to the liquid chamber 500.

The mechanical feature 337c for the liquid bag could project from the front, rear, left side, or right side of the upstanding arm 333. The mechanical feature 337c for holding the liquid bag is advantageously on an opposite face of the arm to the mechanical features 337a, 337b for holding the conduit and/or patient interface such as a cannula in order to balance out the moment and reduce stress on the arm. As described in relation to support assembly 200, the mechanical features 337a, 337b for holding the conduit and/or patient interface such as a cannula may advantageously be on the opposite side of the upstanding arm 333 from the mount 351 to avoid interfering with the breathing assistance apparatus 10 being inserted into or being removed from the mount 351. As such, the mechanical feature 337c for holding the liquid bag may be on the side of the upstanding arm 333 that the breathing assistance apparatus 10 mounts to. The mechanical feature 337c for holding the liquid bag may advantageously be vertically higher than the mechanical features 337a, 337b for holding the conduit and/or patient interface such as a cannula, and as such would have less chance of interfering with the with the breathing assistance apparatus 10 being inserted into or being removed from the mount 351.

Although the liquid bag holder portion 336 is shown in the holder 331 of a support assembly 300 with a conduit and/or patient interface holder portion 335, a mount 351, and a stand 301 comprising a base 303, the liquid bag holder portion 336 could alternatively be used in combination with any of the various designs for other features described in the specification. For example, the liquid bag holder portion 336 and/or the conduit and/or patient interface holder portion 335 could be used in a holder apparatus that mounts to the apparatus 10 such as that shown in FIG. 29, but that does not include a stand/base.

Figure 31:
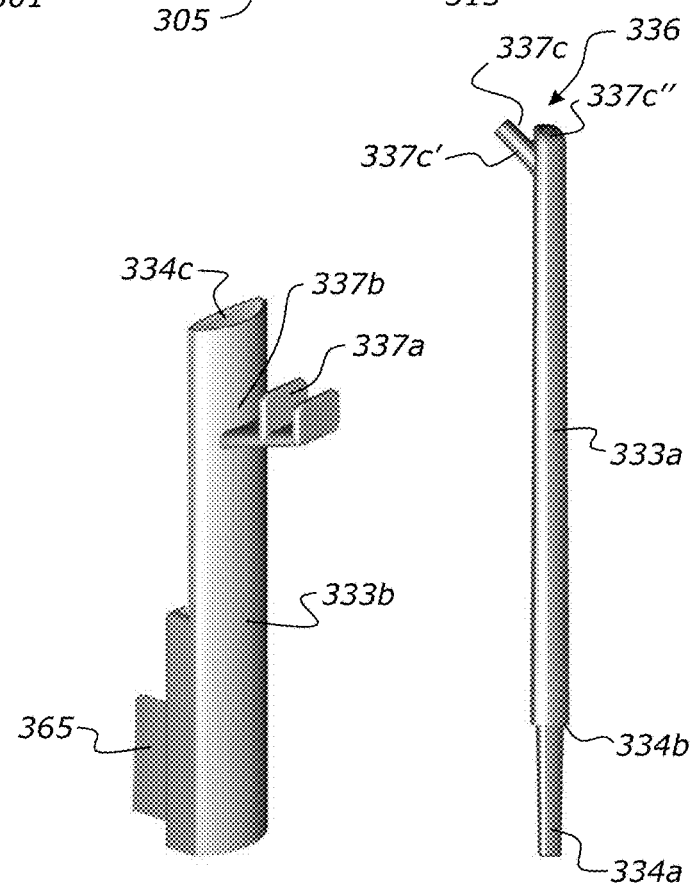
FIG. 31 is an exploded perspective view of components of the conduit and/or patient interface holder of the support assembly of FIG. 30.

The stand 301 and holder 331 could be integrally formed as one piece. Alternatively, certain sections of the support assembly 300 could be releasably coupled to each other. For example, the holder 331 could be releasably coupled to the stand 301 as described for support assembly 200. The conduit and/or patient interface holder portion 335 and the liquid bag holder portion 336 could be integrally formed as part of a one piece upstand arm 333. Alternatively, or in addition, the conduit and/or patient interface holder portion 335 could be formed on a lower part 333b of the upstand arm 333, and the liquid bag holder portion 336 could be formed on an upper part 333a of the upstand arm, and the upper part 333a of the upstand arm may releasably couple to the lower part 333b of the upstand arm. The coupling mechanism for coupling the upper part 333a of the upstand arm to the lower part 333b of the upstand arm could be the same as any of the coupling mechanisms described herein for coupling the holder 231/231' to the stand 201. FIG. 31 illustrates one exemplary configuration in which a tapered member 334a extends downwardly from a lower shoulder 334b on the upper part 333a and is configured for receipt in a cavity 334c in the lower part 333b to releasably mount the upper and lower parts together.

Having multiple members that can be assembled and disassembled offers advantages in terms of easier packaging. Additionally, having the upper part 333a of the holder 331 for holding the liquid bag removable is useful in situations where the user does not want and/or require a liquid bag, such as when using a humidifier that is not designed to be used with a liquid bag. This would allow for removal of the upper part 333a of the upstand arm when not in use to provide a more compact stand and holder apparatus.

In another example, instead of having the mechanical features 237a, 237b for holding the conduit and/or patient interface such as a cannula positioned next to one another, the holder could have two separate features 437a, 437b spaced out vertically, one for holding the patient interface such as a cannula and one for holding the conduit. An exemplary configuration is shown in FIGS. 32 to 35. Unless described below, the features and functionality are otherwise the same as described above for support assembly 200 and 300, and like reference numerals indicate like parts with the addition of 200 and 100 respectively.

Figure 32:
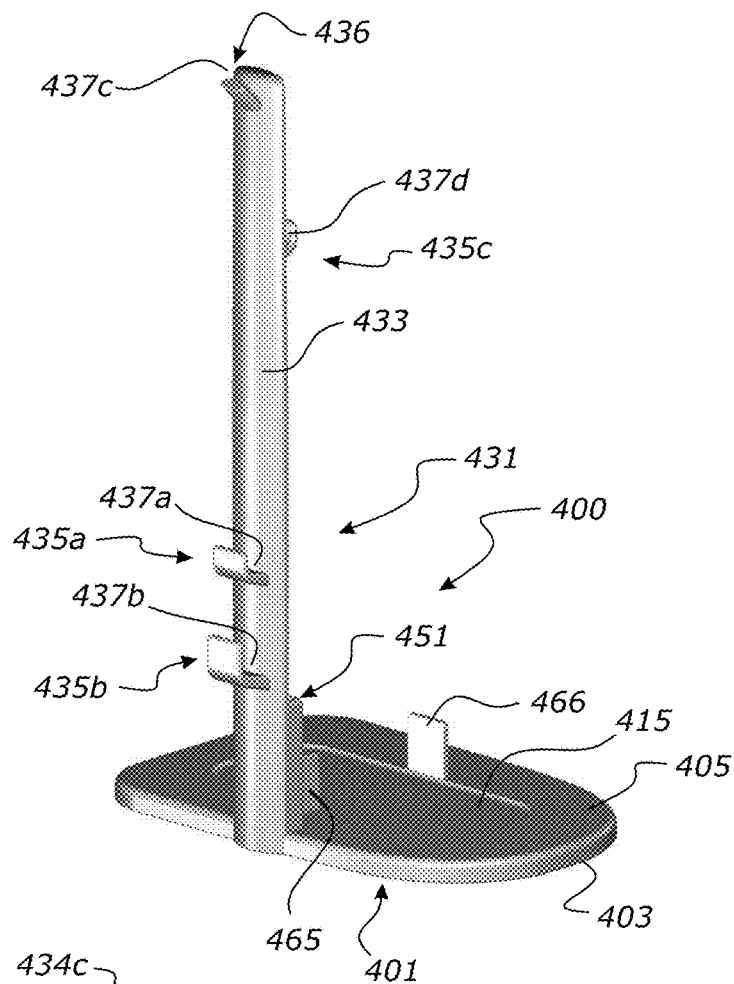
FIG. 32 is a left/front overhead perspective view showing an alternative configuration support assembly for the breathing assistance apparatus and/or a conduit and/or patient interface such as a cannula.
Figure 33:
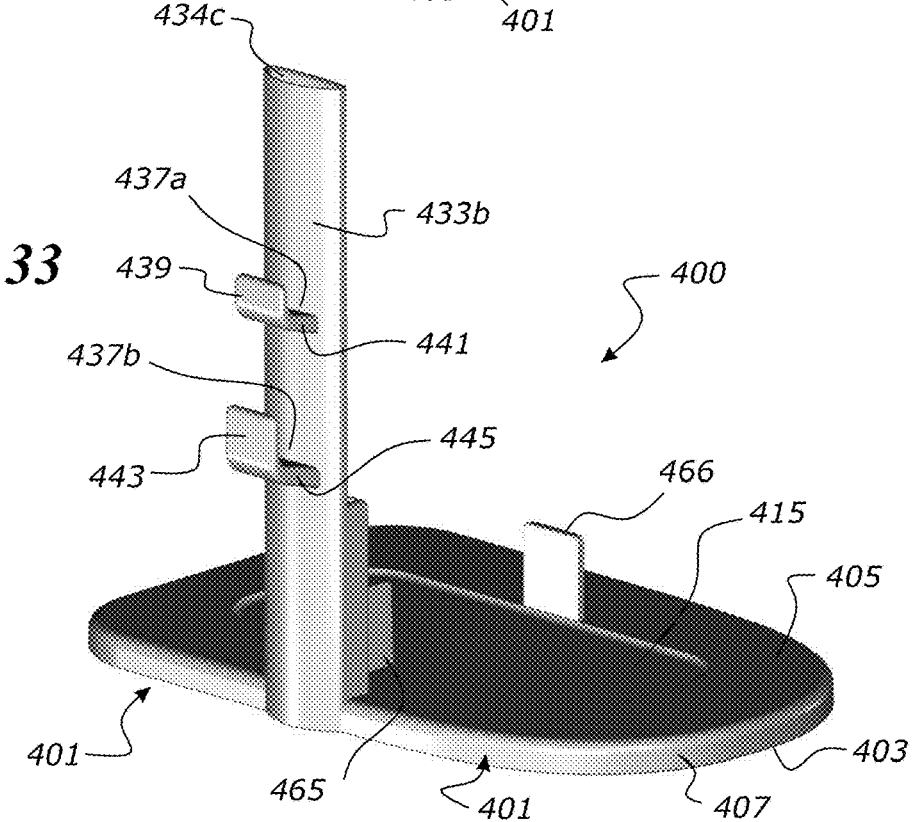
FIG. 33 is a left/front overhead perspective view of the stand and a lower part of the conduit and/or patient interface holder of the support assembly of FIG. 32.

In this configuration, the patient interface holder portion 435a is positioned vertically higher than the conduit holder portion 435b. The patient interface holder portion 435a comprises a mechanical feature 437a for holding the patient interface such as a cannula and the conduit holder portion 435b comprises a mechanical feature 437b for holding the conduit. The mechanical feature 437a for holding the patient interface such as a cannula may be smaller than that for holding the conduit. In FIG. 32, the patient interface holder portion 435a is above the conduit holder portion 435b; however, this could be reversed. The mechanical features 437a, 437b may be located on the outside of the upstand arm 433 to avoid interfering with the breathing assistance apparatus 10 being inserted into or being removed from the mount 451.

A support member in the form of an upwardly projecting member 466 could be located on the opposite side of the base of the stand 401 to further support the breathing assistance apparatus 10 in the desired position with a spacing above the base. The support member 466 could be used in addition to the projecting rib 265, 365, 465, or instead could be used without the projecting rib 265, 365, 465. The upwardly projecting member 466 assists with reducing stress and preventing a large moment being generated at the mount 451. In the form shown, the upwardly projecting member 466 is on an opposite side of the stand 401 to the first projecting rib 465. In an alternative configuration, upwardly projecting member(s) could instead be positioned at or toward a front and/or rear of the stand, but at least half way across the stand 401 from the position of the mount 451. However, having a single upwardly projecting member 466 on the opposite side of the stand is preferred, because it that leaves space available at the front and rear of the stand for inserting accessories into the space between the stand and the breathing assistance apparatus 10. The upwardly projecting member 466 may advantageously be a configuration that has a long dimension in a front-rear direction of the stand 401 and a small dimension in a transverse direction of the stand, to minimise encroachment of the upwardly projecting member 466 into the space under the apparatus 10. Alternatively, the upwardly projecting member could have any other suitable configuration. The upwardly projecting member(s) could be provided in any of the stands 201, 301, 401, 401' described herein.

The upstand arm 433 could have a separate holder portion 435c for holding the patient interface such as a cannula and/or conduit, either in addition to holder portions 435a, 435b or instead of one or both of holder portions 435a, 435b. This feature is illustrated in FIGS. 32 to 35, where the mechanical feature 437c for holding the water bag is on the left and a separate mechanical feature 437d for holding the patient interface such as a cannula and/or conduit is on the right.

The separate mechanical feature 437d for holding the patient interface such as a cannula and/or conduit could be similar to any of the previous described configurations. However, due to the increased vertical distance from the breathing assistance apparatus 10, it may not be necessary to have mechanical features for holding both the patient interface such as a cannula and the conduit. Instead one feature 437d could be used to hold the patient interface such as a cannula, and the increased distance would prevent the conduit from coiling and getting tangled, removing the need for a separate conduit holding mechanical feature 437b. Another option is to have one feature that is used to hold the conduit with the patient interface such as a cannula hanging from the conduit end.

Figure 35:
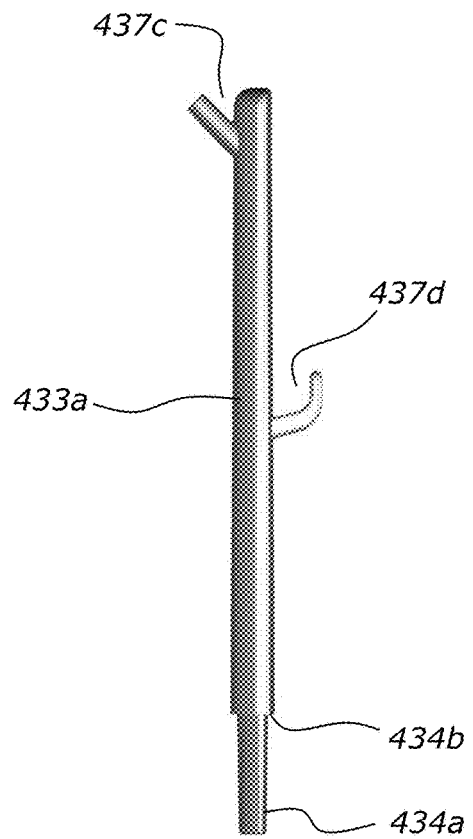
FIG. 35 is a front view of the upper part of the holder of the support assembly of FIG. 32.
Figure 36:
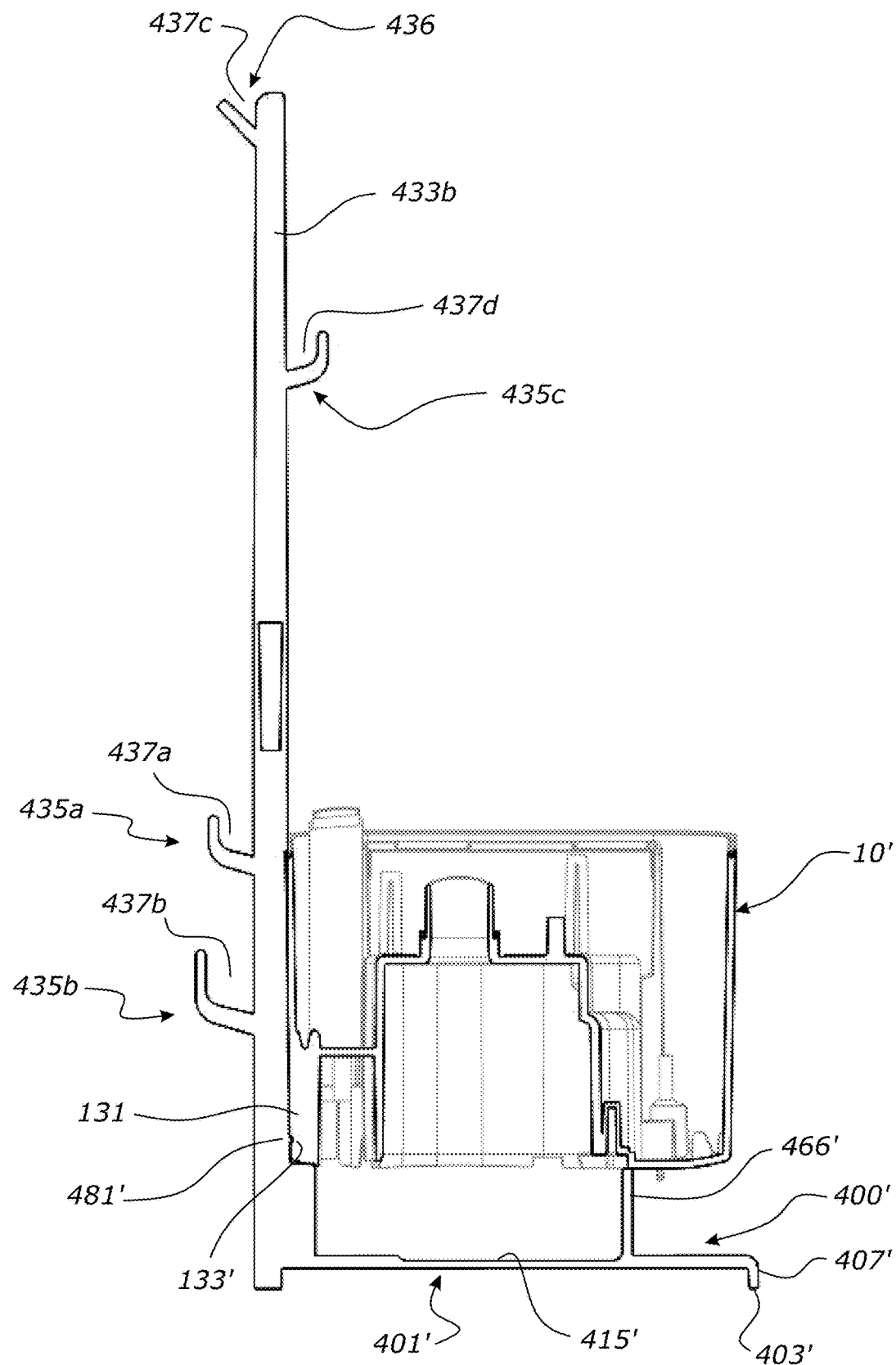
FIG. 36 is a front part sectional view of a breathing assistance apparatus mounted to a support assembly.
Figure 37:
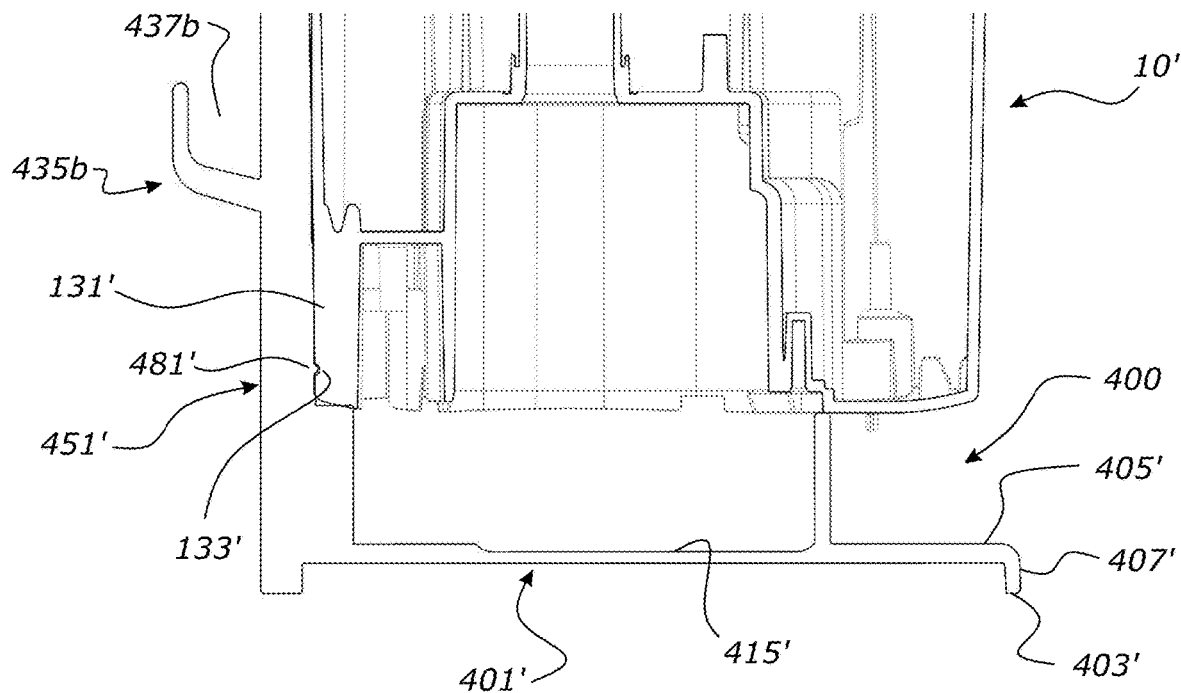
FIG. 37 is a detail view similar to FIG. 36 but showing detail of the engagement of the breathing assistance apparatus and the support assembly.
Figure 38:
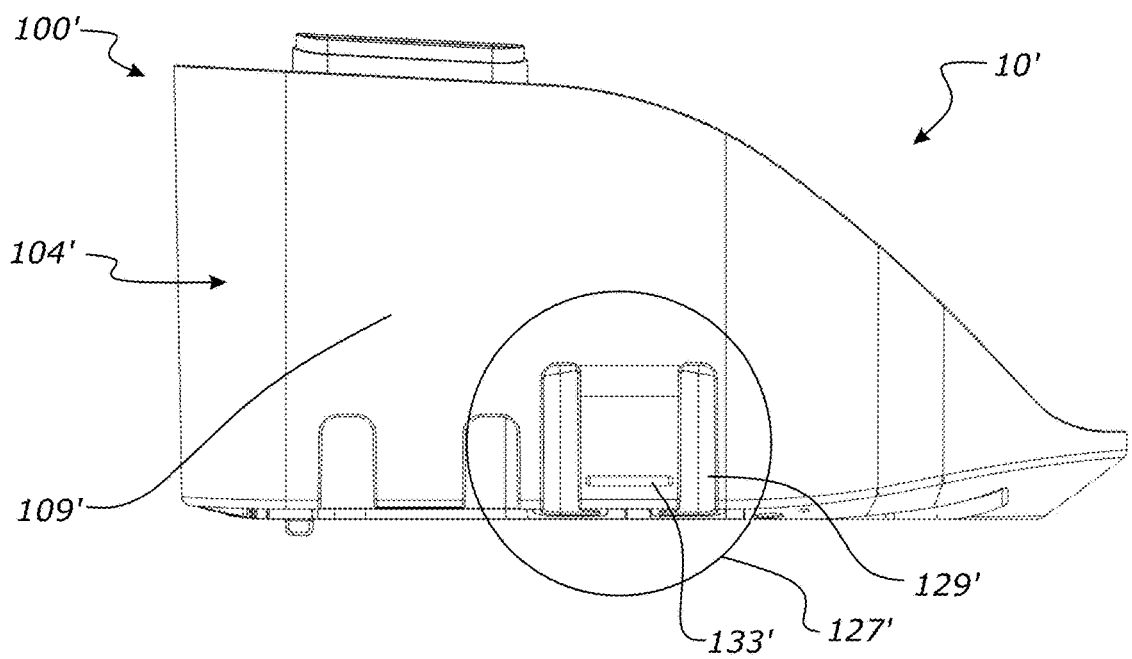
FIG. 38 is a left side view of the breathing assistance apparatus showing the mechanical feature for engaging the breathing assistance apparatus with the support assembly.
Figure 39:
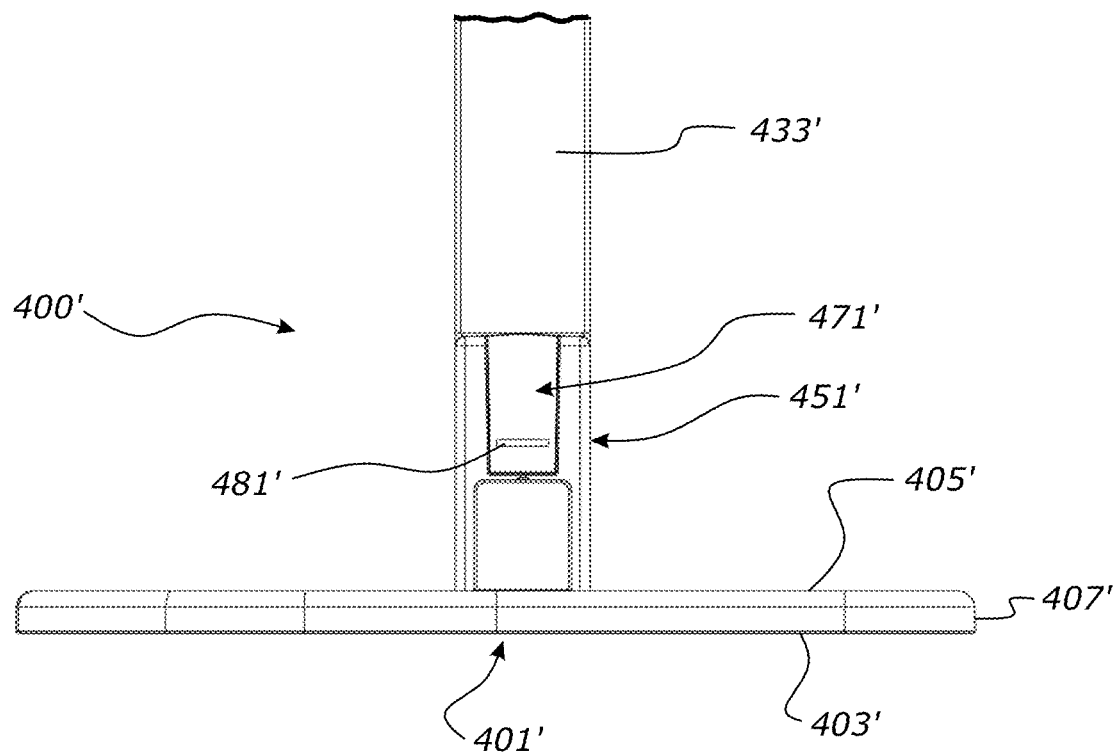
FIG. 39 is a right side view of the support assembly showing the mechanical feature for engaging the support assembly with the breathing assistance apparatus.

The mechanical feature 437c for holding the liquid bag is shown in FIG. 35 to be positioned vertically higher than the mechanical feature 437d for holding the conduit and/or patient interface such as a cannula. Each mechanical feature would be located based on its corresponding accessory, and could be located differently from what is shown. The mechanical feature 437c for holding the liquid bag would likely be as high as possible to provide a vertical distance of the bag above the breathing assistance apparatus 10. The mechanical feature 437d for holding the patient interface such as a cannula would be located based on the length of the conduit.

The assembled form of this configuration is shown in FIG. 32. Due to the large space that the liquid bag would occupy, the mechanical feature 437*d* for holding the patient interface such as a cannula and/or conduit is on the opposite side of the upstand arm 433 to the mechanical feature 437*c* for holding the liquid bag. In the configuration shown, the mechanical feature 437*d* for holding the patient interface such as a cannula is on the same side of the upstand arm 433 as the breathing assistance apparatus, while the mechanical feature 437*c* for holding the liquid bag is on the opposite side of the upstand arm 433. This orientation has a number of advantages. The liquid bag being on the opposite side of the upstand arm from the breathing assistance apparatus prevents the liquid bag from obscuring the display and/or user interface of the breathing assistance apparatus. The patient interface such as a cannula and conduit would only obscure the display and/or user interface when they are hung on the holder and are not in use, and as such the display and/or user interface would not be needed to be used anyway. A full liquid bag will also be heavier than the patient interface such as a cannula and conduit, so putting it opposite the breathing assistance apparatus 10 would best counteract the weight of the breathing assistance apparatus 10. The patient interface such as a cannula would likely be removed more frequently than the liquid bag. Since the support assembly 400 would likely be oriented with the breathing assistance apparatus 10 facing the user, the mechanical feature 437*d* for holding the patient interface such as a cannula is advantageously on this side, so the patient interface such as a cannula is accessible to the user. Having a sufficiently long conduit and a sufficiently high mechanical feature 437*d* would mean that the hanging patient interface such as a cannula and/or conduit, and the mechanical feature 437*d*, should not interfere with insertion and removal of the breathing assistance apparatus 10 onto the mount 451.

Figure 34:
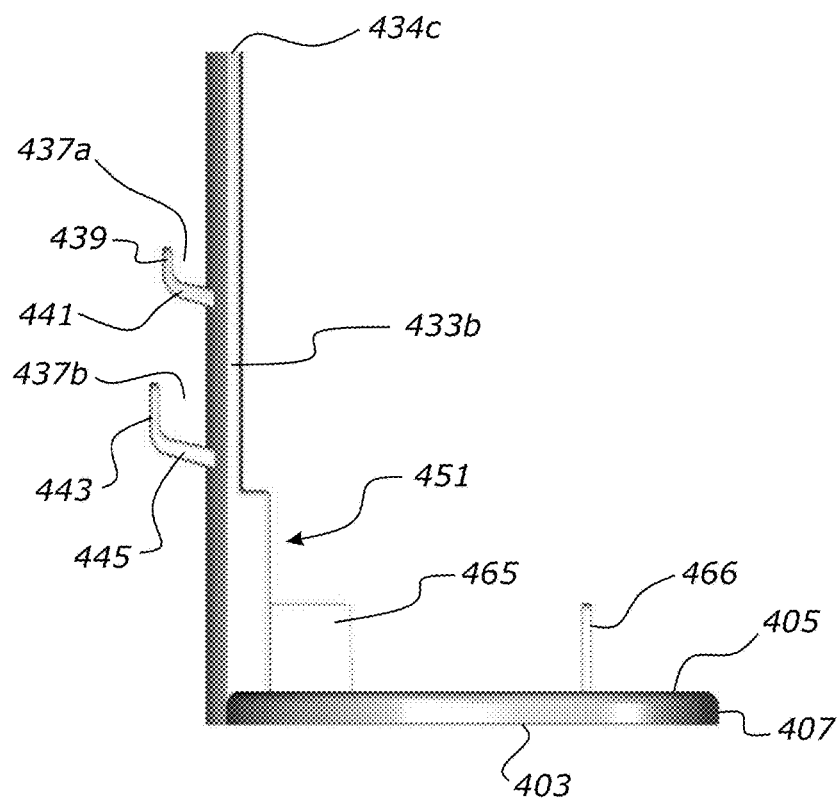
FIG. 34 is a front view corresponding to FIG. 33.

As discussed for support assembly 300, the upper part 433*a* of the upstand member 433 may be removably coupled to the lower part 433*b* of the upstand member 433. This would allow the patient to remove the upper part 433*a* when a liquid bag is not being used. As such, it may be beneficial to have mechanical features 437*a*, 437*b*, 437*d* for holding the patient interface such as a cannula and/or conduit on both the upper part 433*a* and the lower part 433*b* of the upstand member 433, as shown in FIGS. 34 and 35. This would allow for the user to hang the patient interface such as a cannula in the higher position when using the liquid bag holder, but still allow for the patient interface such as a cannula and conduit to be supported when the liquid bag holder is not being used.

Although the liquid bag holder portion 436 and separate conduit and/or patient interface holder portion 435 c are shown in the holder 431 of a support assembly 400 with additional conduit and/or patient interface holder portions 435*a*, 435*b*, a mount 451, and a stand 401 comprising a base 403, those features could alternatively be used in combination with any of the various designs for other features described in the specification. For example, the liquid bag holder portion 436 and/or the separate conduit and/or patient interface holder portion 435*c* could be used in a holder apparatus that mounts to the apparatus 10 such as that shown in FIG. 29, but that does not include a stand/base.

In another example, the support assembly 400' and the breathing assistance apparatus 10' may have optional complementary fastening features that clip the breathing assistance apparatus 10' to the mount 451', to enhance positive engagement between the breathing assistance apparatus 10' and the mount 451'. This would allow the breathing assistance apparatus 10' to be lifted without the support assembly 400' disconnecting and falling out from below it. An exemplary configuration of a support assembly 400' and the breathing assistance apparatus 10' is shown in FIGS. 36 to 39. Unless described below, the features and functionality are otherwise the same as described above for support assembly 400 and breathing assistance apparatus 10, and like reference numerals indicate like parts with the addition of a prime (').

FIG. 25 shows a bump on the outer wall of the apparatus 10 that engages with a corresponding bump on the inner wall of the mount 251. In an alternative configuration, only one of the apparatus 10 and the mount 251 may have a bump. One function of these bumps is to angle the breathing assistance apparatus, as described in the specification. The bumps may be redundant when the upwardly projecting support member 466' is employed in the base 403', as this would support the apparatus 10' in the desired orientation.

In order to provide the clipping feature described above, the breathing assistance apparatus 10' could have an indented portion 133' in the form of a recess that engages with the projecting member or bump 481' on the mount, as shown in FIGS. 36 to 39. The indented portion 133' is positioned on the tongue 131', such that when the breathing assistance apparatus 10' is inserted into the mount 451', the tongue 131' will resiliently flex upon contact with the bump 481'. The tongue 131' will return to its regular unflexed position once the bump 481' engages with the corresponding indented portion 133'. The features is designed such that the force required to disengage the bump 481' from the indented portion 133' is greater than the weight force of the support assembly 400' combined with any potential accessory components attached. The features could alternatively be reversed, with the projecting bump being positioned on the tongue 131' of the breathing assistance apparatus and the corresponding indented portion being located on the mount 451'. With this configuration, the angling function provided by the bumps of FIG. 25 will not be present.

The bump 481' and indented portion 133' could be used in combination with any of the various designs for other features described in the specification.

The support assembly is described with reference to a flow therapy apparatus that is capable of delivering heated and humidified gases to a patient or user. The apparatus may be suitable for treating chronic obstructive pulmonary disease (COPD). The apparatus may be configured to deliver gases to a patient interface at a high flow rate (high flow therapy), particularly nasal high flow therapy.

Alternatively, the support assembly may be used with an apparatus for a different purpose. The apparatus may be a high flow therapy apparatus, or may be a low flow therapy apparatus. For example, the features may be provided in an apparatus for providing continuous positive airway pressure (CPAP), which may deliver gases (humidified or otherwise) at lower flow rates.

The support assembly may alternatively be used with an apparatus that does not require a humidifier and therefore does not require the liquid chamber 500 or chamber bay 108 features. The support assembly has broad applications in other types of gas delivery apparatuses.

The 'flow therapy apparatus' language is intended to cover all such variants.

The support assembly could be configured and used to support any suitable patient interface, such as the patient interfaces described in the Introduction section.

Reference to any prior art in this specification is not, and should not be taken as, an acknowledgement or any form of suggestion that the prior art forms part of the common general knowledge in the field of endeavour in any country in the world.

Where reference is used herein to directional terms such as 'up', 'down', 'forward', 'rearward', 'horizontal', 'vertical' etc, those terms refer to when the apparatus is in a typical in-use position and/or with reference to particular orientations shown in the figures, and are used to show and/or describe relative directions or orientations.

The invention claimed is:

1. A support apparatus for a breathing assistance apparatus comprising:
    a base comprising a top surface and a connection element;
    an upstanding component comprising:
        a first end removably coupled to the base;
        a second end opposite the first end; and
        a mounting portion located proximate to the first end of the upstanding component, wherein the mounting portion comprises an upper mount and a lower mount, wherein a spacing is provided between the base and the upper mount, and the upper mount is configured to releasably couple the support apparatus with the breathing assistance apparatus such that an underside of the breathing assistance apparatus is positioned with a spacing above the top surface of the base, wherein the upper mount is configured to restrain the breathing assistance apparatus in at least two dimensions, wherein the lower mount is configured to engage the connection element and to removably couple the upstanding component to the base; and
    a first part of a coupling mechanism configured to releasably couple the upper mount of the upstanding component with a second part of the coupling mechanism associated with the breathing assistance apparatus, the first part of the coupling mechanism comprising one of a receptacle or a projection, and the second part of the coupling mechanism comprising the other of the receptacle or the projection, wherein the receptacle is configured to receive the projection such that the breathing assistance apparatus is restrained in the at least two dimensions, wherein the receptacle comprises a front wall, a rear wall opposite the front wall, and two opposing side walls extending between the front wall and the rear wall, wherein the receptacle is configured to receive the projection by sliding the projection between the front wall, the rear wall, and the two opposing side walls.

2. The support apparatus according to claim 1, wherein a vertical dimension of the base is smaller than horizontal dimensions of the base, and wherein the top surface of the base comprises a recess for storage of one or more accessories.

3. The support apparatus according to claim 1, wherein the base further comprises a support member spaced from the mounting portion to assist with supporting the breathing assistance apparatus above the top surface of the base.

4. The support apparatus according to claim 1, wherein the base is configured to rest on a surface and support a weight of the breathing assistance apparatus.

5. The support apparatus according to claim 4, wherein the base further comprises an under surface comprising a plurality of strengthening ribs configured to provide strength and rigidity to the base.

6. The support apparatus according to claim 1, wherein the connection element is a spigot and the lower mount comprises a receptacle configured to receive the spigot.

7. The support apparatus according to claim 6, wherein the spigot extends upwardly from the top surface of the base.

8. The support apparatus according to claim 1, wherein the projection comprises a tongue.

9. The support apparatus according to claim 1, wherein the upper mount of the upstanding component comprises the receptacle of the coupling mechanism.

10. The support apparatus according to claim 1, wherein the receptacle further comprises an open end opposite a closed end, wherein the closed end comprises an end wall.

11. The support apparatus according to claim 10, wherein the receptacle is configured to receive the projection by sliding the projection through the open end of the receptacle and between the front wall, the rear wall, and the two opposing side walls until the end of the projection contacts the end wall.

12. The support apparatus according to claim 1, wherein the receptacle comprises a slot extending along the front wall.

13. The support apparatus according to claim 12, wherein the front wall comprises a first portion and a second portion, wherein the first and second portions of the front wall are on opposing sides of the slot.

14. A combination of the support apparatus according to claim 1 and the breathing assistance apparatus releasably coupled to the mounting portion, wherein the underside of the breathing assistance apparatus is positioned with a spacing above the top surface of the base.

15. The combination of claim 14, wherein the spacing is sufficient to provide a storage space for a liquid bag, breathing conduit, and/or power cord of the breathing assistance apparatus.

16. The combination of claim 14, wherein the support apparatus and breathing assistance apparatus comprise complementary fastening features that clip the breathing assistance apparatus to the mounting portion.

17. The combination of claim 16, wherein the complementary fastening features comprise an indented portion on one of the support apparatus and the breathing assistance apparatus, and a complementary projecting portion on the other of the support apparatus and the breathing assistance apparatus.

18. The combination of claim 14, wherein the breathing assistance apparatus comprises the projection of the coupling mechanism.

19. The combination of claim 14, wherein the breathing assistance apparatus comprises a housing and a flow generator, wherein the housing is configured to releasably couple to the upper mount of the upstanding component.

20. The combination of claim 19, wherein the housing of breathing assistance apparatus comprises the projection of the coupling mechanism and the upper mount of the upstanding component comprises the receptacle.

* * * * *